(12) United States Patent
Hinman

(10) Patent No.: US 9,221,179 B2
(45) Date of Patent: Dec. 29, 2015

(54) ARTICULATING MECHANISM

(71) Applicant: Intuitive Surgical Operations, Inc., Sunnyvale, CA (US)

(72) Inventor: Cameron D. Hinman, Woodside, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 44 days.

(21) Appl. No.: 13/865,790

(22) Filed: Apr. 18, 2013

(65) Prior Publication Data

US 2013/0239734 A1    Sep. 19, 2013

Related U.S. Application Data

(63) Continuation of application No. 12/508,478, filed on Jul. 23, 2009, now abandoned.

(51) Int. Cl.
| | |
|---|---|
| *F16C 11/06* | (2006.01) |
| *B25J 17/00* | (2006.01) |
| *A61B 17/29* | (2006.01) |
| *A61B 17/00* | (2006.01) |

(52) U.S. Cl.
CPC .............. *B25J 17/00* (2013.01); *A61B 17/29* (2013.01); *A61B 17/2909* (2013.01); *F16C 11/0614* (2013.01); *A61B 2017/003* (2013.01); *A61B 2017/00314* (2013.01); *A61B 2017/00327* (2013.01); *A61B 2017/291* (2013.01); *A61B 2017/2908* (2013.01); *A61B 2017/2911* (2013.01); *A61B 2017/2925* (2013.01); *A61B 2017/2927* (2013.01); *Y10T 74/20323* (2015.01); *Y10T 403/32* (2015.01); *Y10T 403/32032* (2015.01); *Y10T 403/32639* (2015.01)

(58) Field of Classification Search
CPC .................. F16C 11/0661; A61B 2017/00314
USPC .............. 403/50, 52, 56, 114, 123, 115, 117, 403/112, 113, 116; 606/106, 206
See application file for complete search history.

(56) References Cited

U.S. PATENT DOCUMENTS

| | | | |
|---|---|---|---|
| 1,820,463 A | 8/1931 | Klein | |
| 2,470,210 A * | 5/1949 | Booth | ............................. 403/36 |
| 3,060,972 A | 10/1962 | Sheldon | |

(Continued)

FOREIGN PATENT DOCUMENTS

| | | |
|---|---|---|
| EP | 165718 A2 | 12/1985 |
| EP | 0598618 A2 | 5/1994 |

(Continued)

OTHER PUBLICATIONS

PCT/US10/42685 International Search Report and Written Opinion of the International Searching Authority, mailed Sep. 13, 2010, 7 pages.

(Continued)

*Primary Examiner* — Daniel P Stodola
*Assistant Examiner* — Matthew R McMahon

(57) ABSTRACT

An articulating mechanism is provided with at least one pair of spherical joints interconnected by a set of tension members. Each joint includes a ball member, a socket member configured to pivotably receive at least a portion of the ball member, and at least one tension member extending through both the ball and socket members parallel to and offset from a central longitudinal axis of the joint.

11 Claims, 22 Drawing Sheets

(56) References Cited

U.S. PATENT DOCUMENTS

| | | | |
|---|---|---|---|
| 3,071,161 A | 1/1963 | Ulrich | |
| 3,190,286 A | 6/1965 | Stokes | |
| 3,497,083 A * | 2/1970 | Anderson et al. | 414/738 |
| 3,557,780 A | 1/1971 | Sato | |
| 3,605,725 A | 9/1971 | Bentov | |
| 4,231,672 A * | 11/1980 | Blanpain et al. | 403/62 |
| 4,466,649 A | 8/1984 | Ozawa | |
| 4,489,826 A | 12/1984 | Dubson | |
| 4,580,551 A | 4/1986 | Siegmund et al. | |
| 4,700,693 A | 10/1987 | Lia et al. | |
| 4,763,669 A | 8/1988 | Jaeger | |
| 4,790,294 A | 12/1988 | Allred, III et al. | |
| 4,834,761 A | 5/1989 | Walters | |
| 4,854,626 A | 8/1989 | Duke | |
| 4,880,015 A | 11/1989 | Nierman | |
| 4,949,927 A | 8/1990 | Madocks et al. | |
| 4,984,951 A | 1/1991 | Jameson | |
| 5,046,764 A * | 9/1991 | Kimura et al. | 285/154.2 |
| 5,174,276 A | 12/1992 | Crockard | |
| 5,251,611 A * | 10/1993 | Zehel et al. | 600/141 |
| 5,257,618 A | 11/1993 | Kondo | |
| 5,271,381 A | 12/1993 | Ailinger et al. | |
| 5,273,026 A | 12/1993 | Wilk | |
| 5,286,228 A | 2/1994 | Lee et al. | |
| 5,297,443 A | 3/1994 | Wentz | |
| 5,314,424 A | 5/1994 | Nicholas | |
| 5,322,064 A | 6/1994 | Lundquist | |
| 5,325,845 A | 7/1994 | Adair | |
| 5,330,502 A | 7/1994 | Hassler et al. | |
| 5,354,162 A | 10/1994 | Burdea et al. | |
| 5,381,782 A | 1/1995 | DeLaRama et al. | |
| 5,403,342 A | 4/1995 | Tovey et al. | |
| 5,405,344 A | 4/1995 | Williamson et al. | |
| 5,425,743 A | 6/1995 | Nicholas | |
| 5,441,494 A | 8/1995 | Ortiz | |
| 5,448,989 A * | 9/1995 | Heckele | 600/142 |
| 5,454,827 A | 10/1995 | Aust et al. | |
| 5,476,479 A | 12/1995 | Green et al. | |
| 5,486,154 A | 1/1996 | Kelleher | |
| 5,490,819 A | 2/1996 | Nicholas et al. | |
| 5,498,256 A | 3/1996 | Furnish | |
| 5,513,827 A | 5/1996 | Michelson | |
| 5,520,678 A | 5/1996 | Heckele et al. | |
| 5,522,788 A | 6/1996 | Kuzmak | |
| 5,549,636 A | 8/1996 | Li | |
| 5,562,699 A | 10/1996 | Heimberger et al. | |
| 5,570,919 A | 11/1996 | Eusebe | |
| 5,599,151 A | 2/1997 | Daum et al. | |
| 5,609,601 A | 3/1997 | Kolesa et al. | |
| 5,620,415 A | 4/1997 | Lucey et al. | |
| 5,624,398 A | 4/1997 | Smith et al. | |
| 5,626,608 A | 5/1997 | Cuny et al. | |
| 5,632,432 A | 5/1997 | Schulze et al. | |
| 5,643,294 A | 7/1997 | Tovey et al. | |
| 5,647,743 A | 7/1997 | Schmitt | |
| 5,702,408 A | 12/1997 | Wales et al. | |
| 5,704,534 A | 1/1998 | Huitema et al. | |
| 5,713,505 A | 2/1998 | Huitema | |
| 5,716,352 A | 2/1998 | Viola et al. | |
| 5,749,828 A | 5/1998 | Solomon et al. | |
| 5,759,151 A | 6/1998 | Sturges | |
| 5,792,164 A | 8/1998 | Lakatos et al. | |
| 5,807,376 A | 9/1998 | Viola et al. | |
| 5,813,813 A | 9/1998 | Daum et al. | |
| 5,823,066 A | 10/1998 | Huitema et al. | |
| 5,827,323 A | 10/1998 | Klieman et al. | |
| 5,836,960 A | 11/1998 | Kolesa et al. | |
| 5,845,540 A | 12/1998 | Rosheim | |
| 5,846,183 A | 12/1998 | Chilcoat | |
| 5,873,817 A | 2/1999 | Kokish et al. | |
| 5,899,425 A | 5/1999 | Corey, Jr. et al. | |
| 5,902,254 A * | 5/1999 | Magram | 600/585 |
| 5,916,146 A | 6/1999 | Allotta et al. | |
| 5,916,147 A | 6/1999 | Boury | |
| 5,921,956 A | 7/1999 | Grinberg et al. | |
| 5,938,678 A | 8/1999 | Zirps et al. | |
| 5,947,984 A | 9/1999 | Whipple | |
| 5,961,532 A | 10/1999 | Finley et al. | |
| 6,017,010 A | 1/2000 | Cui | |
| 6,019,722 A | 2/2000 | Spence et al. | |
| 6,042,155 A * | 3/2000 | Lockwood | 285/264 |
| 6,050,996 A | 4/2000 | Schmaltz et al. | |
| 6,161,543 A | 12/2000 | Cox et al. | |
| 6,250,532 B1 | 6/2001 | Green et al. | |
| 6,270,453 B1 | 8/2001 | Sakai | |
| 6,352,227 B1 | 3/2002 | Hathaway | |
| 6,464,704 B2 | 10/2002 | Schmaltz et al. | |
| 6,471,641 B2 | 10/2002 | Sakamoto | |
| 6,471,696 B1 | 10/2002 | Berube et al. | |
| 6,482,149 B1 | 11/2002 | Torii | |
| 6,491,626 B1 | 12/2002 | Stone et al. | |
| 6,571,042 B1 | 5/2003 | Kordahi | |
| 6,626,824 B2 | 9/2003 | Ruegg et al. | |
| 6,635,071 B2 | 10/2003 | Boche et al. | |
| 6,638,213 B2 | 10/2003 | Ogura et al. | |
| 6,638,287 B2 | 10/2003 | Danitz et al. | |
| RE38,335 E | 11/2003 | Aust et al. | |
| 6,641,528 B2 | 11/2003 | Torii | |
| 6,644,532 B2 | 11/2003 | Green et al. | |
| 6,666,854 B1 | 12/2003 | Lange | |
| 6,669,254 B2 | 12/2003 | Thom et al. | |
| 6,676,676 B2 | 1/2004 | Danitz et al. | |
| 6,682,541 B1 | 1/2004 | Gifford, III et al. | |
| 6,743,239 B1 | 6/2004 | Kuehn et al. | |
| 6,746,443 B1 | 6/2004 | Morley et al. | |
| 6,749,560 B1 | 6/2004 | Konstorum et al. | |
| 6,752,823 B2 | 6/2004 | Prestel | |
| 6,764,445 B2 | 7/2004 | Ramans et al. | |
| 6,773,327 B1 | 8/2004 | Felice et al. | |
| 6,817,972 B2 | 11/2004 | Snow | |
| 6,824,548 B2 | 11/2004 | Smith et al. | |
| 6,843,794 B2 | 1/2005 | Sixto, Jr. et al. | |
| 6,858,005 B2 | 2/2005 | Ohline et al. | |
| 6,860,668 B2 | 3/2005 | Ibrahim et al. | |
| 6,902,560 B1 | 6/2005 | Morley et al. | |
| 6,942,613 B2 | 9/2005 | Ewers et al. | |
| 6,945,979 B2 | 9/2005 | Kortenbach et al. | |
| 6,960,162 B2 | 11/2005 | Saadat et al. | |
| 6,960,163 B2 * | 11/2005 | Ewers et al. | 600/114 |
| 6,976,969 B2 | 12/2005 | Messerly | |
| 6,994,700 B2 | 2/2006 | Elkins et al. | |
| 7,090,402 B2 * | 8/2006 | Peet et al. | 384/193 |
| 7,138,976 B1 | 11/2006 | Bouzit et al. | |
| 7,480,600 B2 | 1/2009 | Massie et al. | |
| 7,553,275 B2 | 6/2009 | Padget et al. | |
| 7,682,319 B2 | 3/2010 | Martin et al. | |
| 7,785,325 B1 | 8/2010 | Milbank | |
| 8,205,522 B2 * | 6/2012 | Buckingham et al. | 74/490.04 |
| 8,246,575 B2 * | 8/2012 | Viola | 604/95.04 |
| 2001/0023313 A1 | 9/2001 | Ide | |
| 2001/0042766 A1 | 11/2001 | Ming-Shun | |
| 2002/0096177 A1 | 7/2002 | Toti et al. | |
| 2002/0111604 A1 | 8/2002 | Doyle et al. | |
| 2002/0156497 A1 | 10/2002 | Nagase et al. | |
| 2002/0161281 A1 | 10/2002 | Jaffe et al. | |
| 2002/0177750 A1 | 11/2002 | Pilvisto | |
| 2003/0016989 A1* | 1/2003 | Wentworth et al. | 403/56 |
| 2003/0036748 A1 | 2/2003 | Cooper et al. | |
| 2003/0050649 A1 | 3/2003 | Brock et al. | |
| 2003/0078644 A1 | 4/2003 | Phan | |
| 2003/0109898 A1 | 6/2003 | Schwarz et al. | |
| 2003/0114838 A1 | 6/2003 | O'Neill et al. | |
| 2003/0135204 A1 | 7/2003 | Lee et al. | |
| 2003/0149338 A1 | 8/2003 | Francois et al. | |
| 2003/0153902 A1 | 8/2003 | Doyle et al. | |
| 2003/0229271 A1 | 12/2003 | Briscoe et al. | |
| 2003/0233026 A1 | 12/2003 | Saadat et al. | |
| 2004/0044350 A1 | 3/2004 | Martin et al. | |
| 2004/0054322 A1 | 3/2004 | Vargas | |
| 2004/0138529 A1* | 7/2004 | Wiltshire et al. | 600/144 |
| 2004/0138700 A1 | 7/2004 | Cooper et al. | |
| 2004/0236316 A1 | 11/2004 | Danitz et al. | |
| 2005/0090809 A1 | 4/2005 | Cooper et al. | |
| 2005/0096694 A1 | 5/2005 | Lee | |

(56) References Cited

U.S. PATENT DOCUMENTS

| | | |
|---|---|---|
| 2005/0107667 A1 | 5/2005 | Danitz et al. |
| 2005/0119527 A1 | 6/2005 | Banik et al. |
| 2005/0186022 A1 | 8/2005 | Garraffa |
| 2005/0251112 A1 | 11/2005 | Danitz et al. |
| 2005/0273084 A1* | 12/2005 | Hinman et al. .................. 606/1 |
| 2005/0273085 A1 | 12/2005 | Hinman et al. |
| 2006/0009759 A1 | 1/2006 | Chrisitian et al. |
| 2006/0020287 A1 | 1/2006 | Lee et al. |
| 2006/0036255 A1 | 2/2006 | Pond, Jr. et al. |
| 2006/0058582 A1 | 3/2006 | Maahs et al. |
| 2006/0094931 A1 | 5/2006 | Danitz et al. |
| 2006/0111209 A1 | 5/2006 | Hinman et al. |
| 2006/0111210 A1 | 5/2006 | Hinman |
| 2006/0111615 A1 | 5/2006 | Danitz et al. |
| 2006/0111616 A1 | 5/2006 | Danitz |
| 2006/0199999 A1 | 9/2006 | Ikeda et al. |
| 2006/0201130 A1 | 9/2006 | Danitz |
| 2007/0250113 A1 | 10/2007 | Hegeman et al. |
| 2007/0276430 A1 | 11/2007 | Lee et al. |
| 2007/0287993 A1 | 12/2007 | Hinman et al. |
| 2008/0065116 A1 | 3/2008 | Lee et al. |
| 2008/0188869 A1 | 8/2008 | Weitzner et al. |
| 2008/0188871 A1 | 8/2008 | Smith et al. |
| 2008/0255421 A1 | 10/2008 | Hegeman et al. |
| 2008/0255588 A1 | 10/2008 | Hinman |
| 2008/0255608 A1 | 10/2008 | Hinman et al. |
| 2008/0262538 A1 | 10/2008 | Danitz et al. |
| 2009/0156995 A1* | 6/2009 | Martin et al. .............. 604/95.04 |
| 2010/0041945 A1 | 2/2010 | Isbell, Jr. |
| 2010/0234831 A1 | 9/2010 | Hinman et al. |
| 2010/0249759 A1 | 9/2010 | Hinman et al. |
| 2010/0261964 A1 | 10/2010 | Danitz et al. |
| 2010/0261971 A1 | 10/2010 | Danitz et al. |
| 2010/0262075 A1 | 10/2010 | Danitz et al. |
| 2010/0262161 A1 | 10/2010 | Danitz et al. |
| 2010/0262180 A1 | 10/2010 | Danitz et al. |
| 2011/0022078 A1 | 1/2011 | Hinman |

FOREIGN PATENT DOCUMENTS

| | | |
|---|---|---|
| EP | 0836833 A2 | 4/1998 |
| EP | 1132041 A2 | 9/2001 |
| EP | 1395398 B1 | 1/2006 |
| JP | 6262549 A2 | 9/1994 |
| JP | 2001299768 A2 | 10/2001 |
| WO | WO-0110292 A1 | 2/2001 |
| WO | WO-0213682 A1 | 2/2002 |
| WO | WO-2004019769 A1 | 3/2004 |
| WO | WO-2004105578 A2 | 12/2004 |
| WO | WO-2005067785 A2 | 7/2005 |
| WO | WO-2005120326 A2 | 12/2005 |
| WO | WO-2005120327 A2 | 12/2005 |
| WO | WO-2006057699 A1 | 6/2006 |
| WO | WO-2006057700 A1 | 6/2006 |
| WO | WO-2006057702 A2 | 6/2006 |
| WO | WO-2006073581 A2 | 7/2006 |

OTHER PUBLICATIONS

Cox J.L., "The Minimally Invasive Maze-III Procedure," Operative Techniques in Thoracic and Cardiovascular Surgery, W.B. Saunders Company, U.S, 2000, vol. 5 (1), pp. 79-92.

Prasad S.M., et al., "Epicardial Ablation on the Beating Heart: Progress Towards an Off-Pump Maze Procedure," The Heart Surgery Forum, Forum Multimedia Publishing, LLC, U.S, 2002, vol. 5 (2), pp. 100-104.

Simha P.M., et al., "The Elctrocautery Maze—How I Do It," The Heart Surgery Forum, Forum Multimedia Publishing, LLC, U.S, 2001, vol. 4 (4), pp. 340-345.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

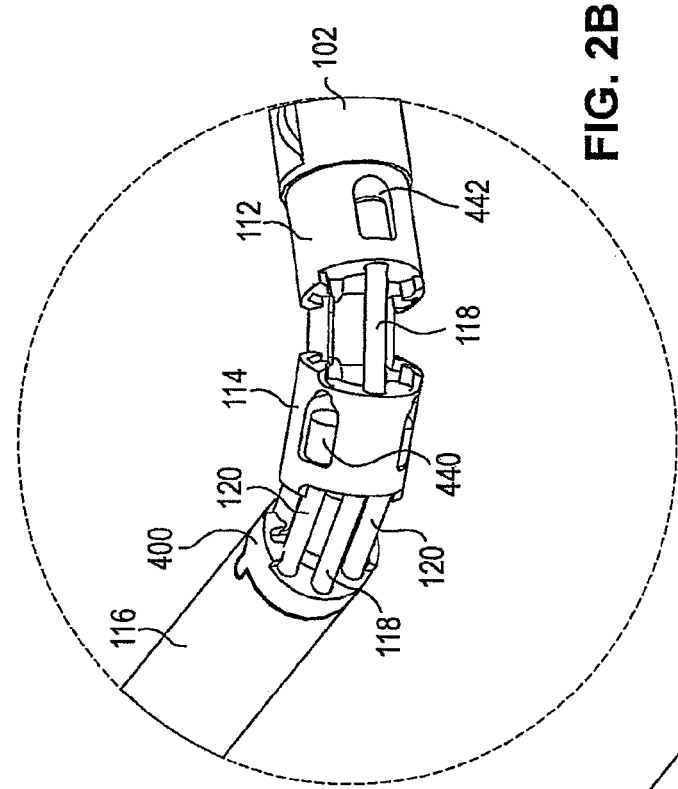
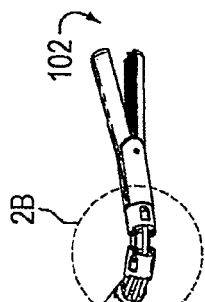
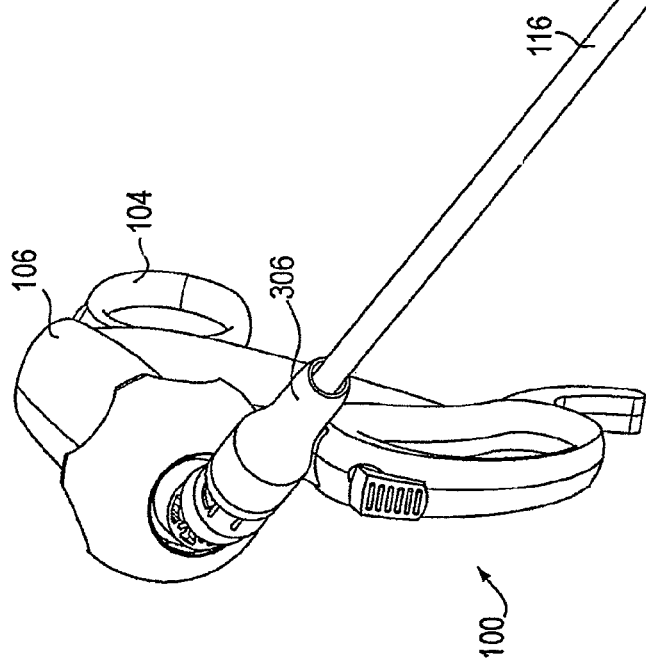

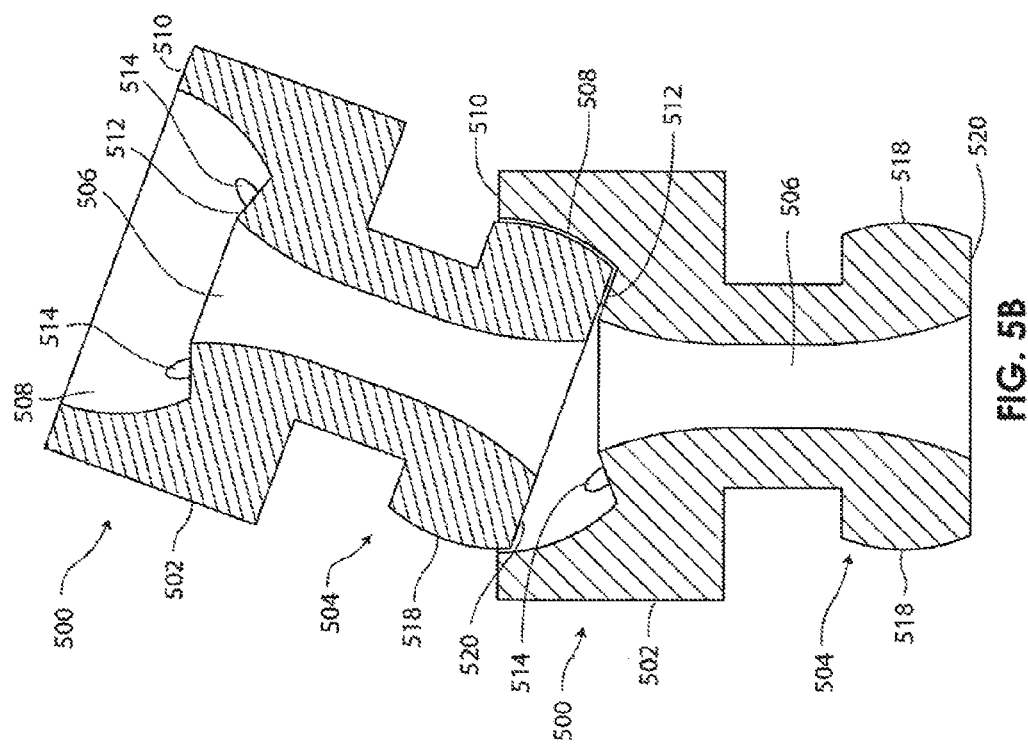
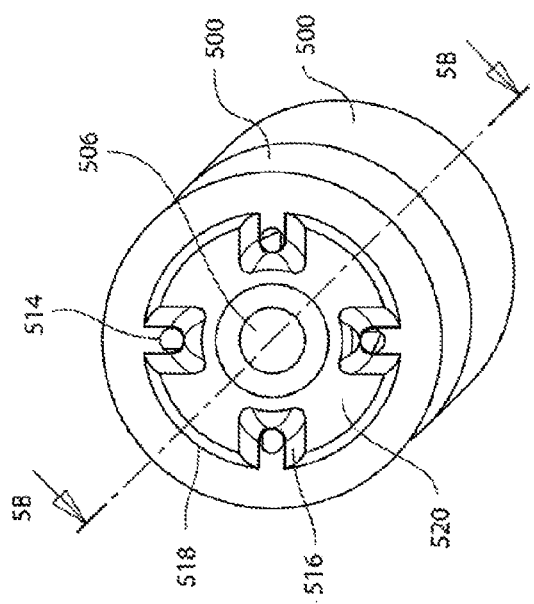

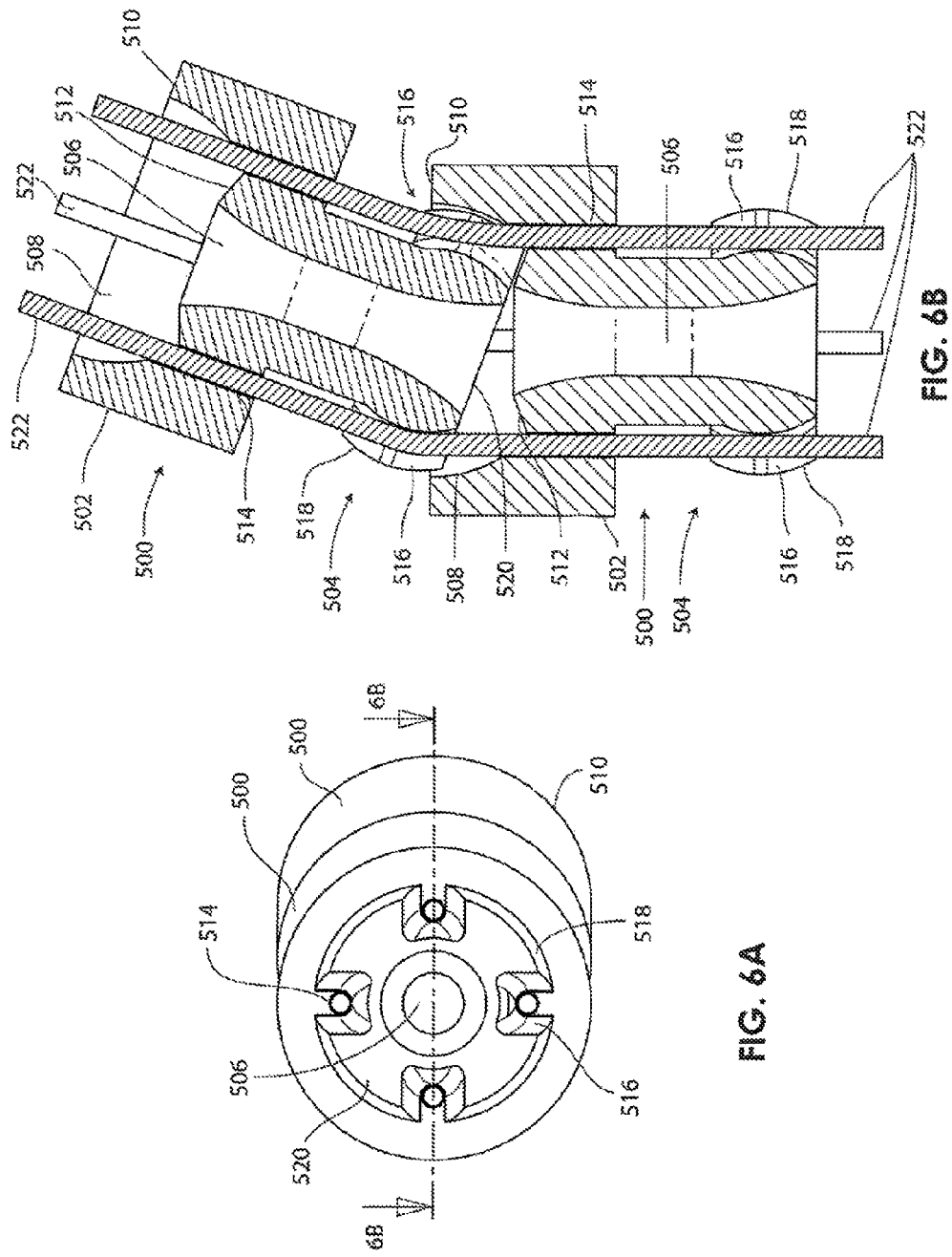

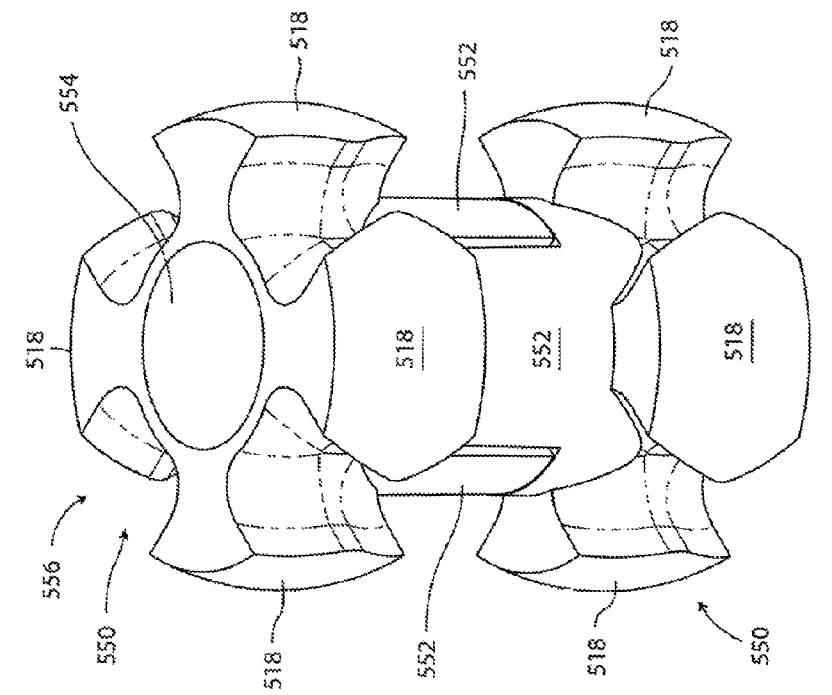
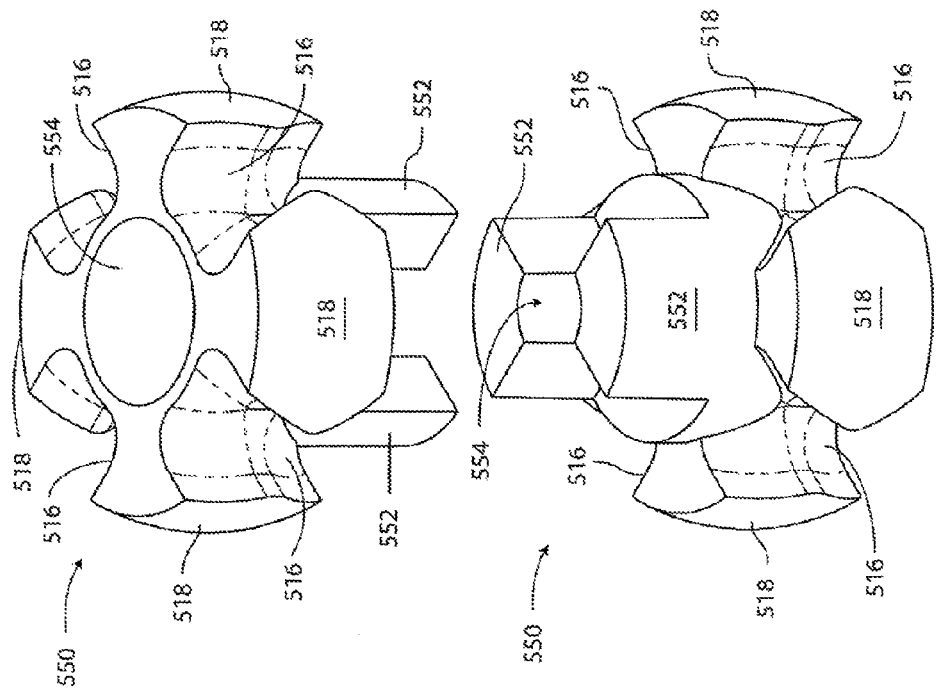

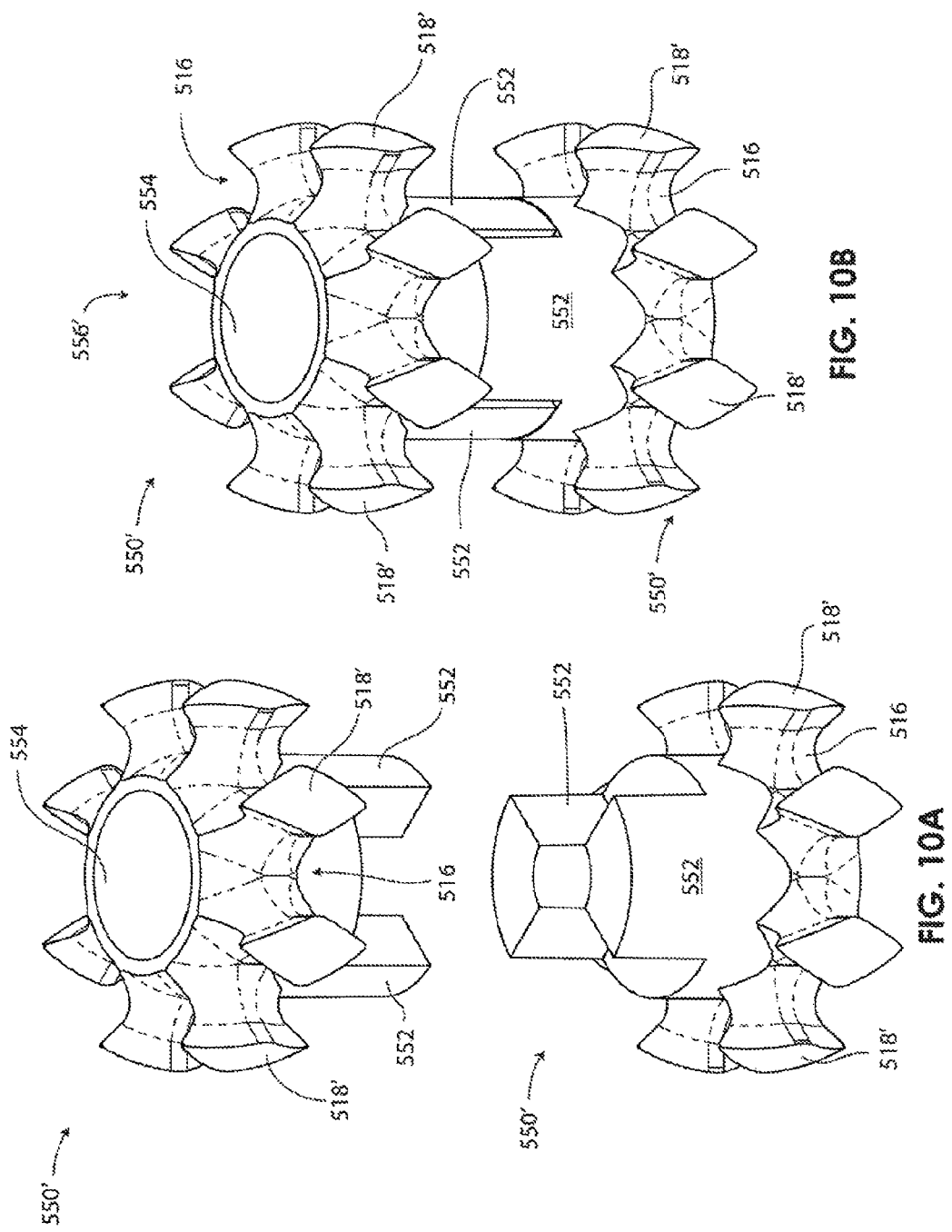

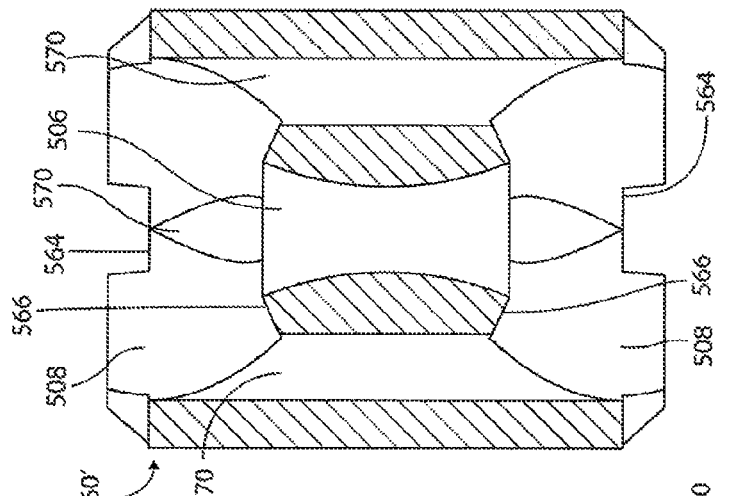
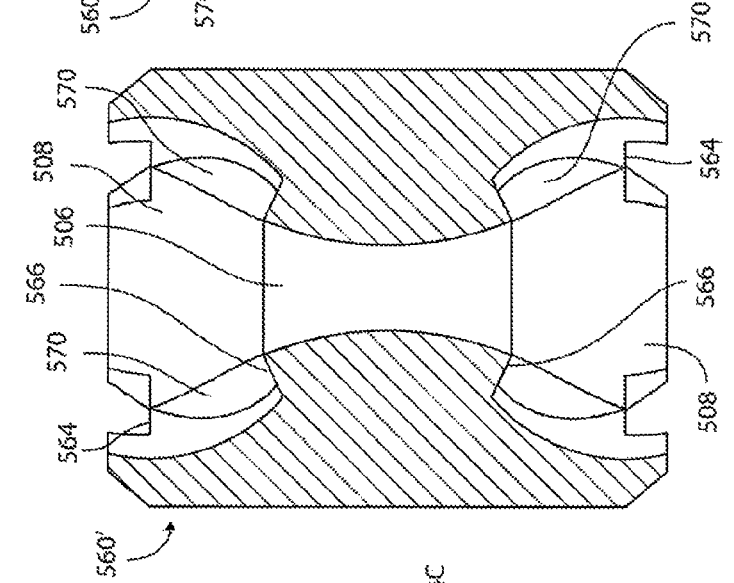
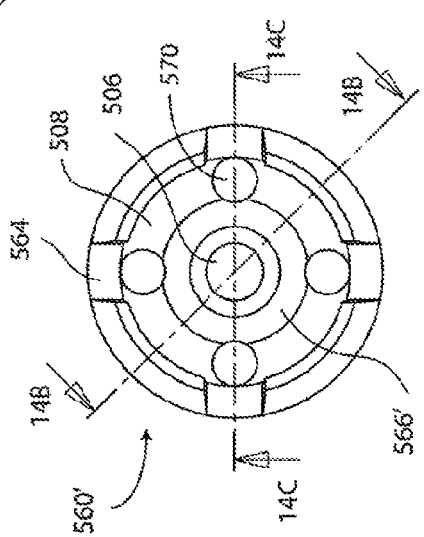
FIG. 14C
FIG. 14B
FIG. 14A

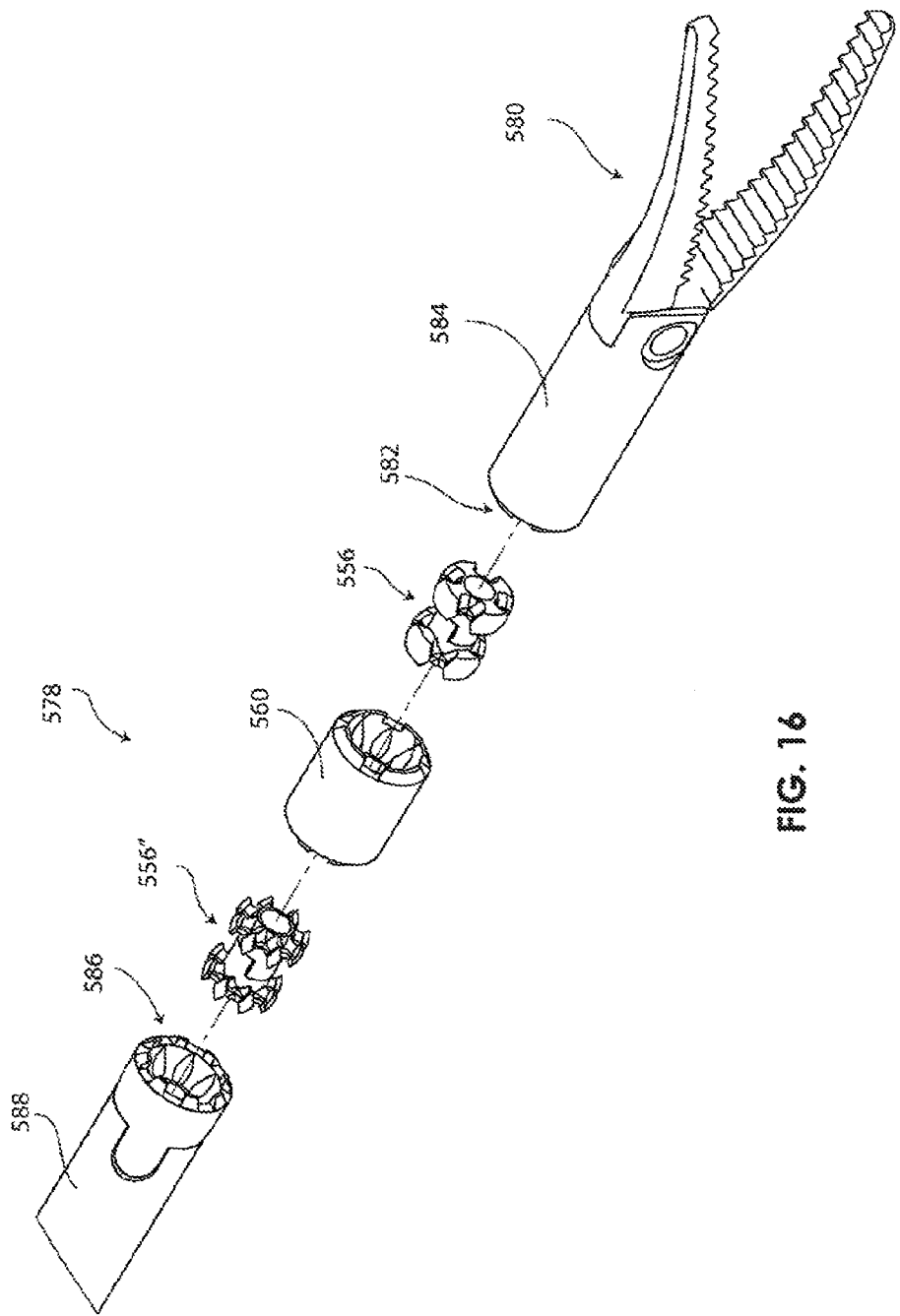

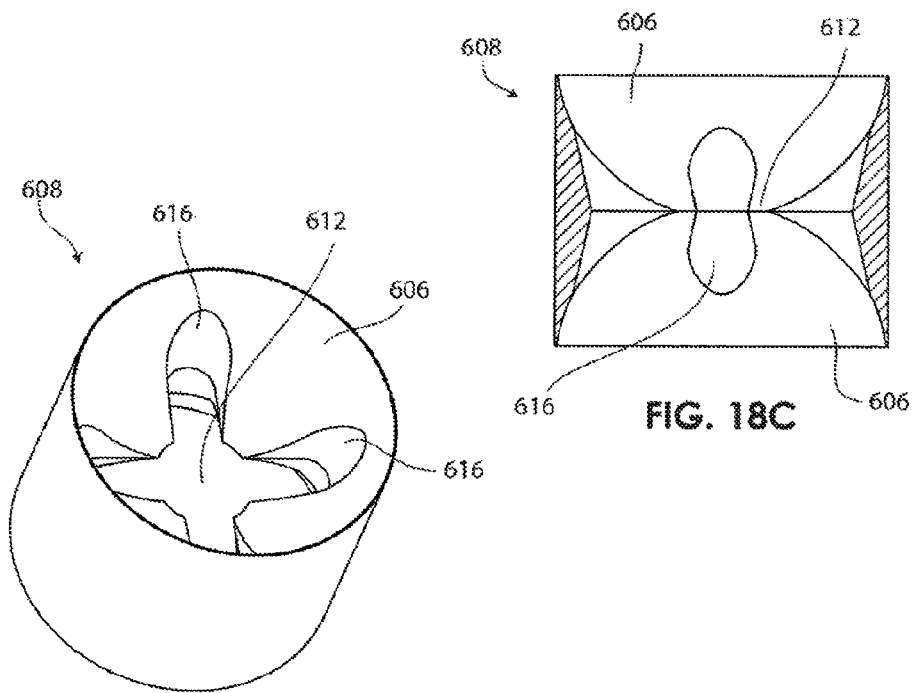
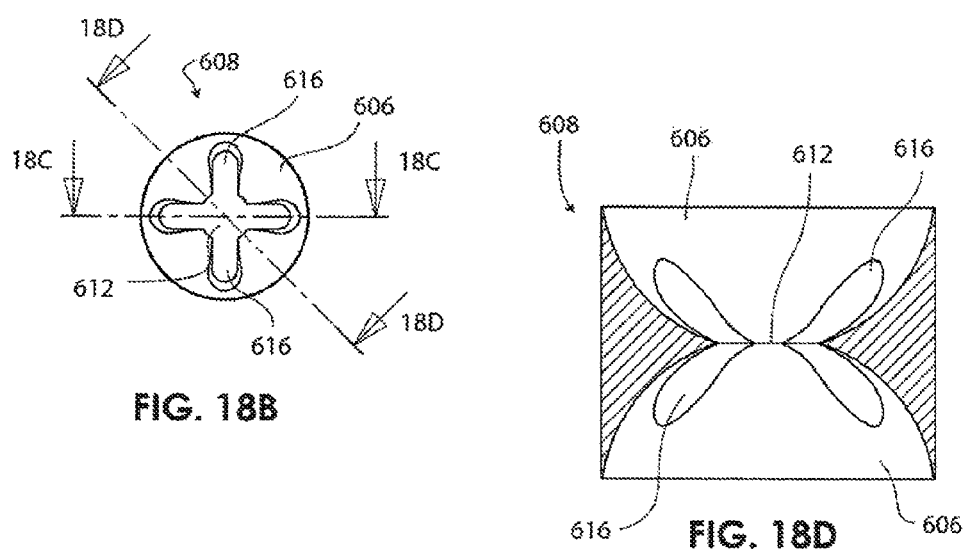

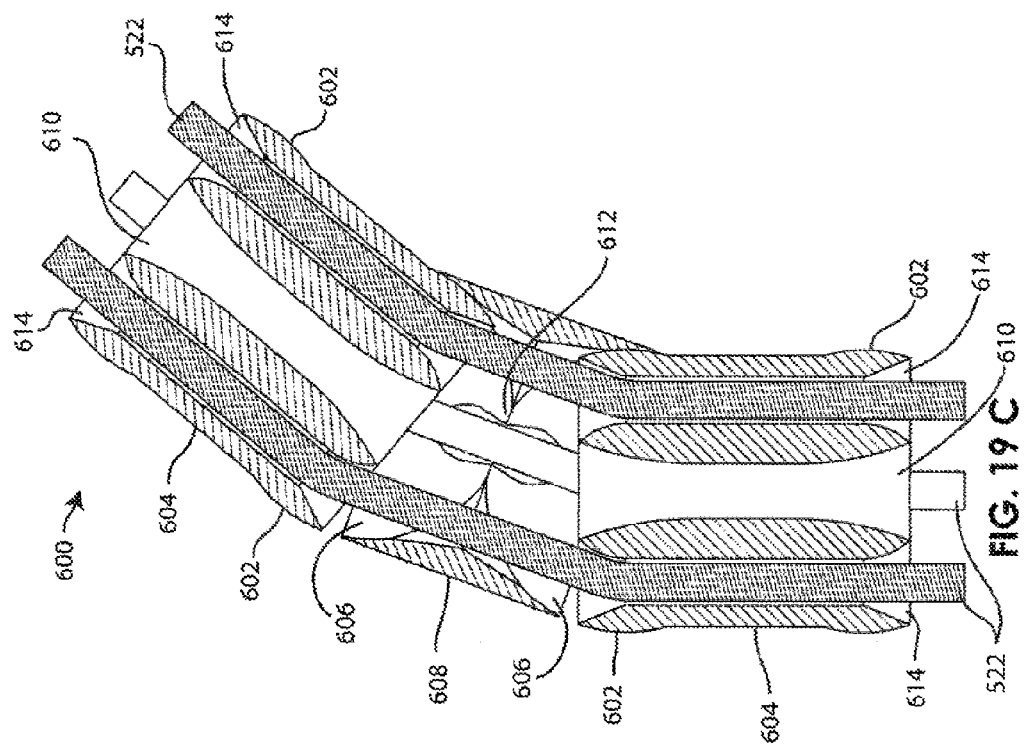
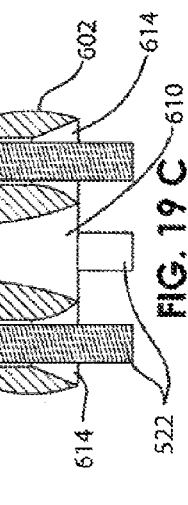
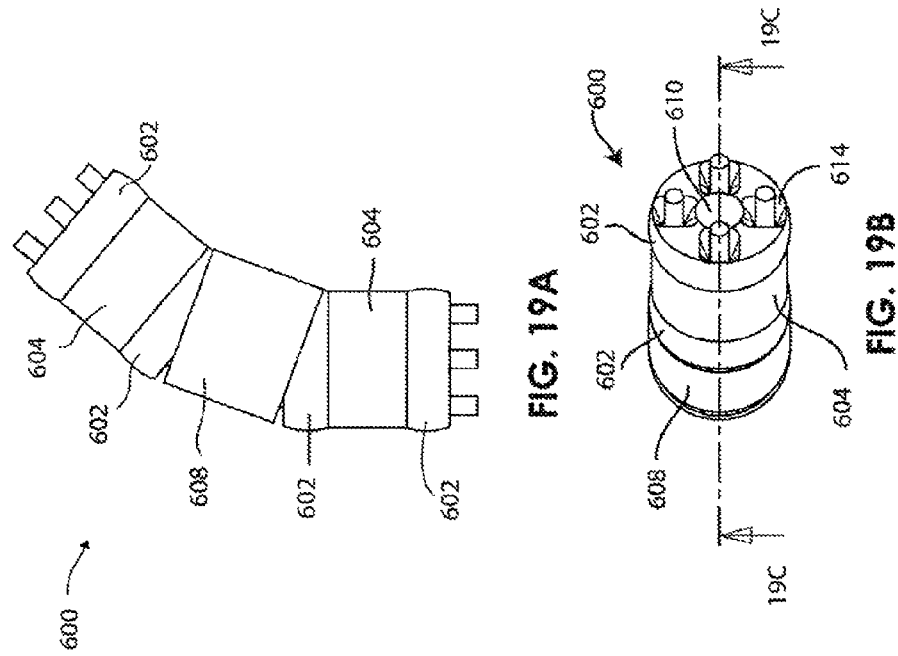

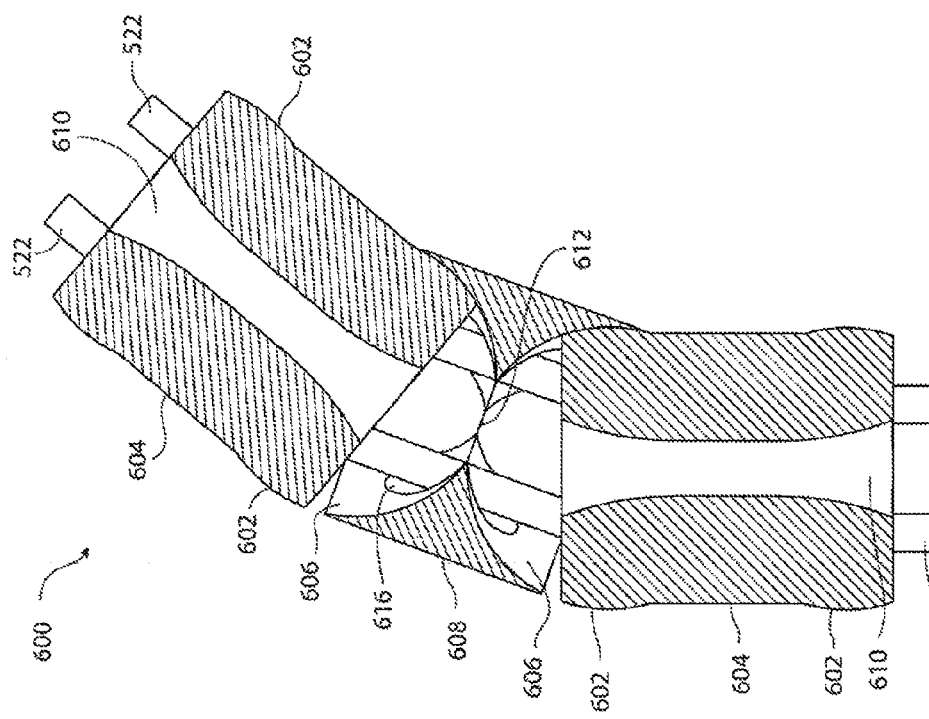
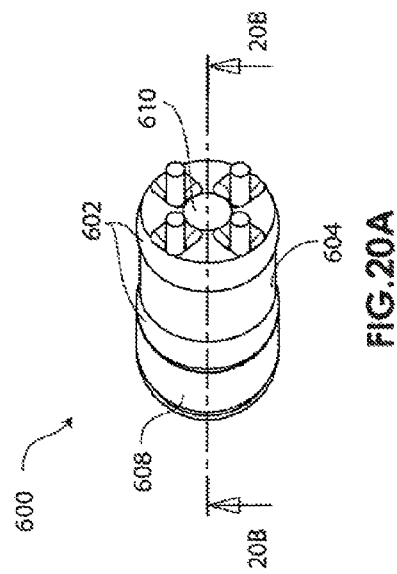
FIG. 20A
FIG. 20B

ARTICULATING MECHANISM

FIELD OF THE INVENTION

This invention relates to articulating mechanisms and applications thereof, including the remote guidance and manipulation of surgical or diagnostic tools.

BACKGROUND OF THE INVENTION

Surgical procedures such as endoscopy and laparoscopy typically employ instruments that are steered within or towards a target organ or tissue from a position outside the body. Examples of endoscopic procedures include sigmoidoscopy, colonoscopy, esophagogastroduo-denoscopy, and bronchoscopy, as well as newer procedures in natural orifice transluminal endoscopic surgery ("NOTES"). Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues.

Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures.

Steerable catheters are also well known for both diagnostic and therapeutic applications. Similar to endoscopes, such catheters include tips that can be directed in generally limited ranges of motion to navigate a patient's vasculature. There have been many attempts to design endoscopes and catheters with improved steerability. For example, U.S. Pat. No. 3,557,780 to Sato; U.S. Pat. No. 5,271,381 to Ailinger et al.; U.S. Pat. No. 5,916,146 to Alotta et al.; U.S. Pat. No. 6,270,453 to Sakai, and U.S. Pat. No. 7,147,650 to Lee describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), by a pulley mechanism (Sato), or by manipulation of complementary portions (Lee). U.S. Pat. No. 5,916,147 to Boury et al. discloses a steerable catheter having four wires that run within the catheter wall. Each wire terminates at a different part of the catheter. The proximal ends of the wires extend loosely from the catheter so that the physician may pull them. The physician is able to shape and thereby steer the catheter by selectively placing the wires under tension.

Recently, surgical instruments, including minimally invasive surgical instruments, have been developed that are more ergonomic and which have a wider range of motion and more precise control of movement. These instruments may include mechanisms that articulate using a series of links coupled with one or more sets of tension bearing members, such as cables. As with conventional instruments used in minimally invasive surgery, rotation of the shaft and end effector with respect to the handle is also an important feature of cable and link type instruments to aid with dissecting, suturing, retracting, knot tying, etc. The links, joints, and other components of existing instrument articulation mechanisms include various undesirable limitations. With the increasing complexity associated with surgical procedures that these instruments are used to perform, further improvements in the design of the articulation mechanisms of the instruments are desirable.

SUMMARY OF THE INVENTION

According to aspects of the invention, articulating tools are provided with improved articulating mechanisms as well as methods of assembling such tools. In some embodiments, the articulating tool is appropriate for multiple uses, including medical uses such as diagnostic and surgical uses.

In some embodiments, an articulating mechanism comprises at least one pair of longitudinally spaced apart spherical joints. Each joint may include a convex component and a mating concave component. The concave component is configured to receive at least a portion of the convex component. Both components may have spherical surfaces adapted to slide relative to one another. The articulating mechanism further comprises at least one set of tension members interconnecting one component of one of the joints of a pair to one component of the other joint of the pair. With this arrangement, movement of one of the interconnected components causes corresponding relative movement of the other interconnected component directly through tension member movement. Each of the convex and concave components includes a plurality of channels. Each channel is sized to slidably receive one of the tension members. Each channel on at least one of the components has an opening located on the spherical surface of the component. The channels located in mating convex and concave components form pairs of opposing channels. At least one of these pairs of opposing channels cooperates with a common tension member received therein to transmit torque between the mating components.

In some of the above embodiments, the articulating mechanism further comprises at least two pairs of longitudinally spaced apart spherical joints. Each of the pairs may have a discrete set of tension members associated with it. The mechanism may further comprise an intermediate member such that each pair of joints has one joint on one side of the member and one joint on the other side of the member. The intermediate member may comprise a rigid tube configured for receiving the tension members therethrough. The convex component of one of the joints may be integrally formed as a single part with the concave component of another of the joints. The convex component of one of the joints may be integrally formed as a single part with the convex component of another of the joints. The concave component of one of the joints may be integrally formed as a single part with the concave component of another of the joints.

In some of the above embodiments, at least one of the convex members comprises a truncated sphere. At least one of the convex members may comprise a frusto-sphere. At least one of the channels may open radially outward through a circumferential edge of the component. In some embodiments, each of the convex and concave components comprises a central axial bore therethrough. In some embodiments, at least one mating pair of convex and concave components has exactly 4 tension member channels running through each component, and/or at least one mating pair of convex and concave components has exactly 8 tension member channels running through each component. The channels in at least one concave component may be radially interconnected to form a cross-pattern.

According to aspects of the invention, a spherical joint may be provided that comprises a ball member, a socket member and at least one tension member. The socket member may be configured to pivotably receive at least a portion of the ball member. The tension member(s) may extend through both the ball and socket members parallel to and offset from a central longitudinal axis of the joint.

In some embodiments, an articulating mechanism for remote manipulation of a surgical or diagnostic tool is provided. The tool may comprise multiple pairs of links. Each link of each pair may be maintained in a spaced apart relationship relative to the other link of the pair. The mechanism may further comprise multiple sets of tension members. Each set of tension members may connect the links of a discrete pair to one another, such that movement of one link of a pair causes corresponding relative movement of the other link of the pair. Each link may be part of a spherical joint having mating convex and concave surfaces. The tension members may extend through channels in the mating surfaces.

In some of the above embodiments, the links form proximal and distal ends with links of corresponding pairs being located adjacent to the proximal and distal ends, respectively. In these embodiments, movement of the proximal end results in corresponding relative movement of the distal end. The articulating mechanism may further comprise a handle located at the proximal end and a grasper at the distal end.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings which are briefly described below.

FIG. 2 shows the device of FIG. 1 in a proximal-looking view, with the handle and end effector in an articulated position. FIG. 2B is a detailed view of the circled portion of FIG. 2A, which includes distal links and bushings.

FIGS. 4A, 4B, 4C, 4D, 4E, 5A, 5B and 6A, 6B show details of a combination link and busing member for use with the articulating device.

FIGS. 7A, 7B and 8A, 8B, 8C, 8D, 8E show details of convex bushing components for use with the articulating device.

FIGS. 10A, 10B and 11A, 11B show details of another convex bushing component for use with the articulating device.

FIG. 14A, 14B, 14C shows details of another concave link member for use with an articulating device.

FIGS. 15-16 show details of an articulating mechanism located on the distal end of an instrument according to aspects of the invention.

FIGS. 17A, 17B, 17C, 17D, 17E, 18A, 18B, 18C, 18D, 19A, 19B, 19C, and 20A, 20B show details of an alternative articulating mechanism.

DETAILED DESCRIPTION OF THE INVENTION

Articulating tools are described in U.S. Pat. No. 7,090,637; US 2005/0107667; US 2005/0273084; US 2005/0273085; US 2006/0111209, US 2006/0111210, and US 2006/0111615. The articulating mechanisms of the tools described in those publications use multiple pairs of segments or links controlled, e.g., by multiple sets of cables, as well as tools that have a single pair of links, connected by a single set of cables, such as those described in U.S. Pat. No. 5,916,146. Depending upon the specific design of the device, the links can be discrete segments (as described, e.g., in U.S. Pat. No. 7,090,637) or discrete portions of a flexible segment (as described, e.g., in US 2005/0273085). The instrument may also include steerable or controllable links, e.g., as described in US 2005/0273084, US 2006/0111209 and US 2006/0111210. The devices of this invention may include optional end effectors at their distal ends and end effector actuators supported by a handle at their proximal ends. When using such articulating instruments, a user may manipulate the proximal end of the instrument, thereby moving one or more distal links of the articulation mechanism. Aspects of the present invention may be used in any of these and in other articulating mechanisms.

Figures 1A, 1B:
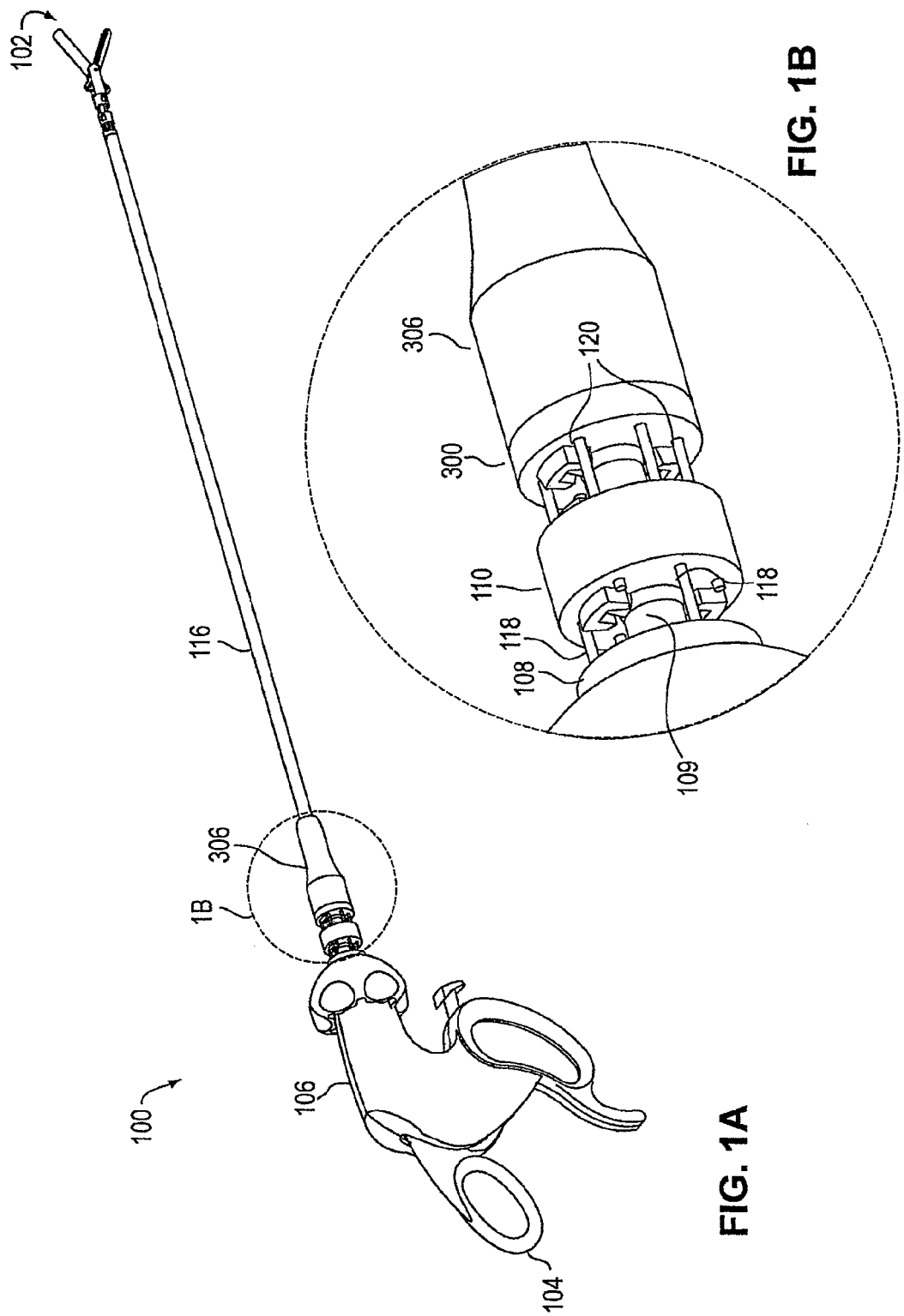
FIG. 1A is an obliquely distal-looking perspective view of an exemplary articulating device having a handle and an end effector.
FIG. 1B is a detailed view of the circled portion of FIG. 1A, which includes proximal links and bushings.

FIGS. 1A and 2A show an exemplary articulatable tool 100 with an end effector 102 at its distal end and an end effector actuator 104 within a handle 106 at its proximal end: FIG. 1A shows the tool in a neutral or non-articulated configuration, while FIG. 2A shows the tool in an articulated position or configuration. FIG. 1B shows detail (encircled in FIG. 1A) of the proximal links of the tool. FIG. 2B shows detail (encircled in FIG. 2A) of the distal links of the tool. Instrument 100 may be used, e.g., in a laparoscopic procedure requiring grasping or cutting within a patient. Exemplary embodiments of the tool 100 may also be useful in endoscopic procedures, particularly when, as in some embodiments, the tool has a flexible shaft. Still other embodiments may be used for percutaneous procedures, such as a catheter. Still other embodiments include devices that are directed toward natural orifice transluminal endoscopic surgery ("NOTES"). Embodiments of the invention may include a wide variety of tools, some with medical or diagnostic purposes, and others that are applied to other types of tasks where the articulational capabilities of the tool provide benefit.

Proximal articulation links 108 and 110 extend distally from handle 106, and distal articulation links 112 and 114 extend proximally from end effector 102. Proximal link 108 is a spindle and is connected to and moves with handle 106. Likewise, distal link 112 is connected to and moves with end effector 102. An elongated shaft 116 is disposed between the proximal links and the distal links; in some embodiments the shaft is rigid, in other embodiments the shaft may be flexible.

A set of tension bearing elements or control cables 118 is attached to proximal link 108, extends through proximal link 110, shaft 116 and distal link 114 and is attached to distal link 112, as shown in FIGS. 1A and 1B. A second set of tension bearing element or control cables 120 is attached to proximal link 110, extends through shaft 116 and is attached to distal link 114. In this embodiment, there are three control cables 118 in the first set and three control cables 120 in the second set. It should be appreciated, however, that other numbers of control cables may be used to connect corresponding proximal and distal links. In addition, tension bearing elements other than cables may be used to connect corresponding links. In some embodiments, the tension members may comprise cables that are capable of only transmitting tension between the links. In other embodiments, the tension members may comprise Nitinol wires, rods or other elements capable of transmitting both tension and compression. In these latter embodiments, a link may be alternately pushed and pulled by at least one tension member. In some embodiments, one set of control cables, such as cables 120, may be eliminated to provide an instrument with a single pair of connected links. What is meant by the word "connected" is that the cable(s) are attached to a pair of links to allow one link to drive another link, as opposed to the cables merely slidably passing through the connected links.

As shown in FIGS. 1A, 1B, 2A, and 2B, movement of handle 106 and proximal link 108 with respect to proximal link 110 moves end effector 102 and distal link 112 in a relative and corresponding manner. Likewise, movement of proximal link 110 with respect to shaft 116 moves distal link 114 with respect to shaft 116 in a relative and corresponding manner, also as shown in FIG. 2. This relative articulation movement provides a way for a user to remotely manipulate the end effector through movement of the handle. It should be understood that the proximal and distal links can be connected by the tension bearing elements so as to move in the same direction with respect to the shaft (thereby providing a mirror image movement) or in opposite directions with respect to the shaft, depending on whether the tension bearing elements connect the corresponding links on the opposite sides or on the same sides of the links, respectively. In addition, the degree of relative movement can be determined by the relative diameters of the cables' connections to corresponding links as well as through the use and specific design of bushings or spacer links separating the connected proximal and distal links. For example, in the embodiment shown in FIGS. 1-3, the cables' radial spacing on the proximal links is about three times greater than their radial spacing on the distal links. This means that a movement of about 5° in a proximal link will cause a corresponding movement of about 15° in a distal link. Further details of these links are provided in US2005/0273085, which is hereby incorporated by this reference.

In the embodiment illustrated in FIG. 1, the end effector 102 is a pair of jaws. Actuation force is transmitted from end effector actuator 104 through a transmission that includes a linearly movable rod and a rotatable rod actuator (not shown). Other end effectors (surgical, diagnostic, etc.) and end effector actuators may be used with an articulating tool constructed according to this invention. In some embodiments, the distal links themselves can comprise an end effector, such as, for example, a retractor. The movable rod may comprise any flexible material; in some embodiments Nitinol offers particular advantages as it is sufficiently flexible to accommodate articulation, and yet can still carry a compressive load sufficiently, for example, to be able to push open an end effector, such as a set of jaws. In some embodiments, a series of proximal links, themselves, can comprise a "handle" with no other rigid handle being provided. In other words, the proximal links may be formed into a particular shape which is emulated by a corresponding series of distal links. More details of such embodiments are provided in U.S. Pat. No. 7,090,637.

Figure 3:
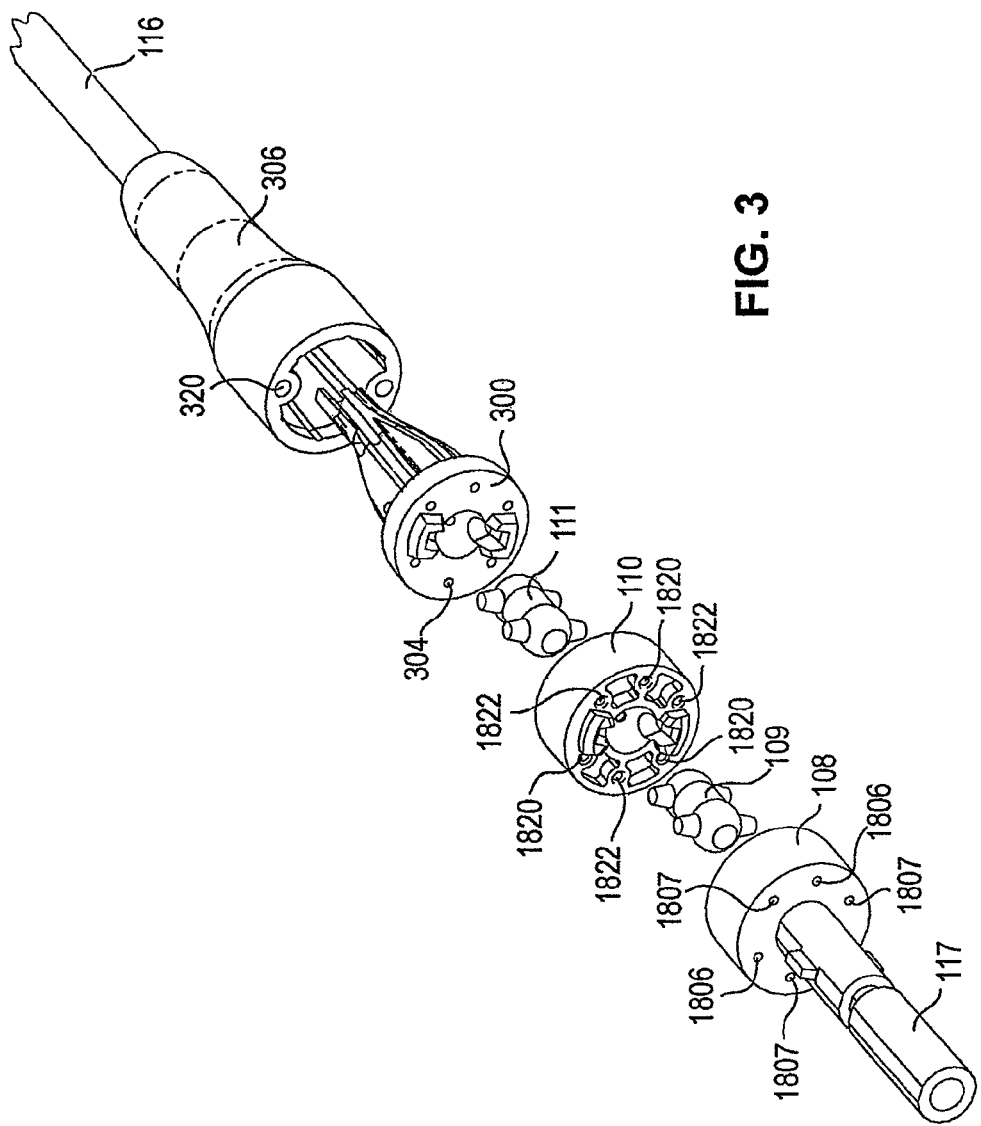
FIG. 3 is an exploded perspective view of certain proximal components of the articulating device.

FIG. 3 shows an exploded view of certain proximal components of the articulating tool. The tension members have been omitted for clarity. As shown, a double headed bushing 109 is disposed between links 108 and 110, and another bushing 111 is disposed between links 110 and a proximal end cap 300. The interaction of bushings 109 and 111 with links 108 and 110 and with proximal end cap 300 is described in more detail in U.S. 2005/0273084, U.S. 2006/0111209, and U.S. 2006/0111210. If the tension bearing cables 118 and 120 were shown in FIG. 3 as they are in FIGS. 1 and 2, the proximal ends of the three cables 118 would terminate in openings 1806 of link 108, and the cables would pass through openings 1820 in link 110 and openings 304 in end cap 300 before entering shaft 116. Likewise, the proximal ends of three cables 120 would terminate in openings 1822 of link 110 and would pass through openings 304 in proximal end cap 300 before entering shaft 116. A tapered end cap housing or cover 306 may be rigidly fixed to shaft 116 to provide a transition from end cap 300 to shaft 116.

As previously noted, device 100 shown in FIGS. 1-3 includes two pairs of links, each interconnected by its own set of tension members. Specifically, one pair is formed by proximal link 108 and distal link 112 which are interconnected by tension members 118, and another pair is formed by proximal link 110 and distal link 114 which are interconnected by tension members 120. In other embodiments, only a single pair of links interconnected by a single set of tension members is used. In yet other embodiments, three or more pairs of links may be used, each interconnected by a discrete set of tension members. In some embodiments, instead of a set of tension members, only a single tension member may be used between a pair of links, such as when the tension member is capable of also transmitting compression between the links.

As shown in FIG. 3, proximal links 108 and 110 are separated by bushing 109, and proximal link 110 is separated from proximal end cap 300 by bushing 111. Proximal bushings 109 and 110 each have a convex spherical component or ball located at each of their ends. Mating concave recesses are formed in proximal links 108 and 110 and in proximal end cap 300 for receiving a portion of the ball ends of the bushings. With this arrangement, proximal links 108 and 110 pivot relative to one another about two pivot points (i.e. about the centers of the two ball ends of bushing 109). Similarly, proximal link 110 and end cap 300 pivot relative to one another about two pivot points (i.e. about the centers of the two ball ends of bushing 111). In other embodiments, some of which are later described, links may pivot relative to one another about a single pivot point. In the embodiment shown in FIG. 3, protruding pin features are located on opposite sides of each ball and are pivotably received within mating slots located in the concave recesses. This pin and slot configuration allows torque to be transmitted across the four proximal spherical joints. Distal links 112 and 114, and distal end cap 400 are separated by bushings in a similar arrangement. As can be seen by the radial location of tension member channels 1806, 1807, 1820, 1822 and 304 relative to the concave recesses, the tension members travel axially along lines that are radially outside of the spherical joint surfaces in this embodiment.

FIGS. 4A-4E show details of a combination link and bushing member 500 that may be used in any of the articulating devices described above. For example, member 500 may be used to replace link 110 and bushing 111 shown in FIG. 3, and a component similar to member 500 may be used to replace link 108 and bushing 109.

Link and bushing member 500 comprises a concave component 502 and a complementary-shaped convex component 504, which may be integrally formed therewith as shown. A central axial bore 506 may be provided through member 500. Concave component 502 includes a recess having a concave spherical surface 508. In this embodiment, spherical surface 508 is bounded above by rim surface 510 and below by stop surface 512, which is further described below. Concave spherical surface 508 is interrupted by the upper openings of four channels 514 that travel axially through the concave component and in this embodiment are evenly spaced around the central axial bore 506.

Figure 4A:
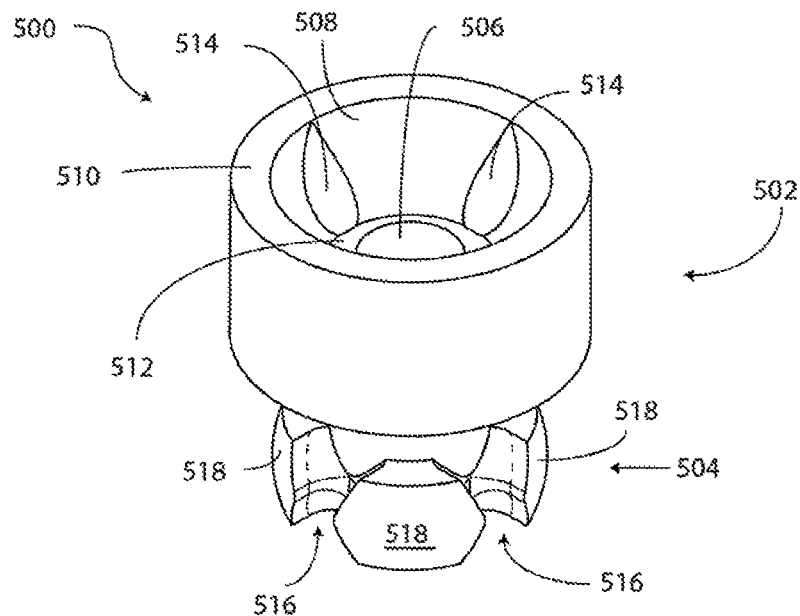
Figure 4B:
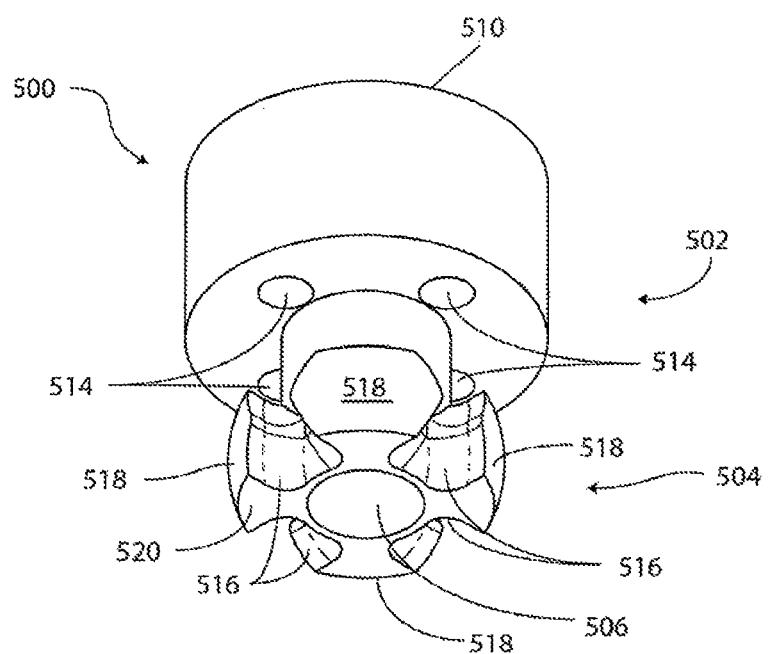
Figure 4C:
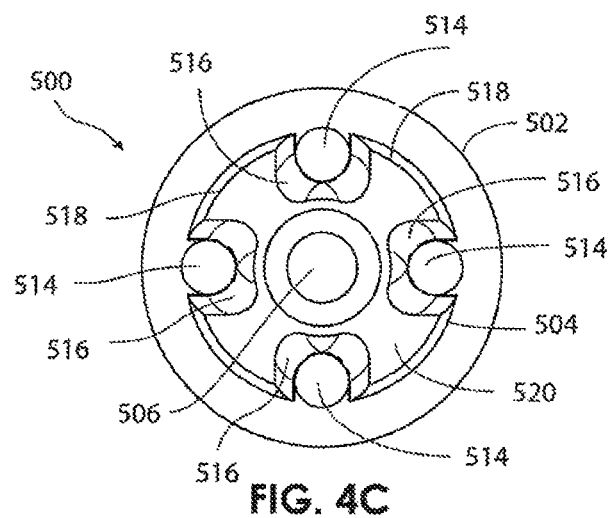
Figure 4D:
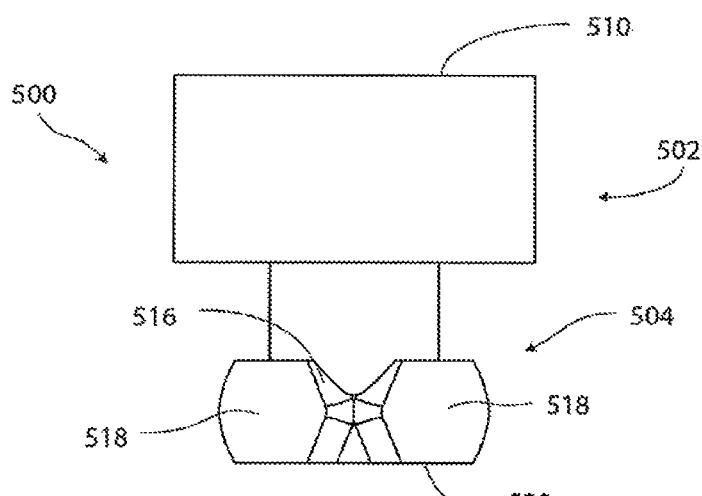
Figure 4E:
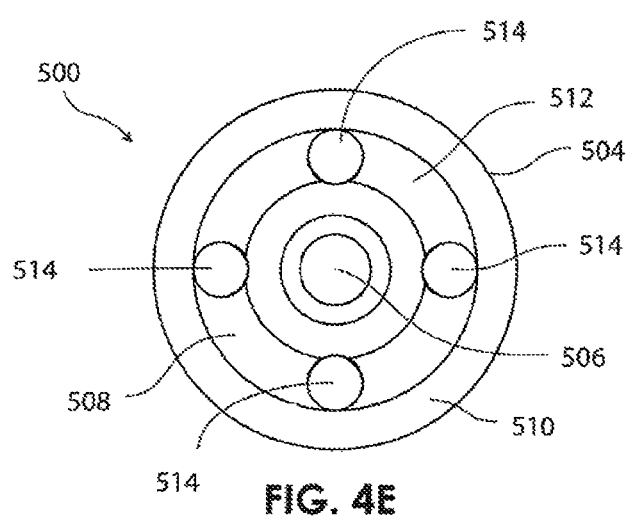

The convex component of member 500 includes a portion having the overall shape of a frustro-sphere, as best seen in FIG. 4D. This frusto-sphere is circumferentially interrupted by four channels 516 that extend axially in line with channels 514, but also extend radially outward to divide the frustro-sphere into four convex spherical surfaces 518. As best seen in FIG. 4D, each channel 516 is outwardly tapered at both its top and bottom to generally form an hourglass shape.

FIGS. 5A-5B show two link and bushing members 500, 500 axially coupled together in operation. As can be seen in FIG. 5B, the convex component 504 of the upper member 500 is received within the concave component 502 of the lower member 500 to form a spherical joint. In this embodiment, the spherical joint is capable of pivoting in at least two degrees of freedom. Dimensions may be appropriately chosen such that the four convex spherical surfaces 518 slidably engage with the concave spherical surface 508 but lateral movement between the spherical surfaces is generally prevented. Stop surface 512 may be provided in the lower concave component for abutting against the bottom surface 520 of the upper convex component to limit the degree of angular rotation permitted between the two members 500, 500. In some embodiments, the degree of angular rotation permitted by stop surface 520 is symmetrical about the central longitudinal axis, and in other embodiments it is asymmetrical. As shown, each central axial bore 506 may be tapered at its top and bottom such that any cables, tubes, fiber optics, etc. passing through the bore are not pinched and do not inhibit members 500, 500 from pivoting.

FIG. 6B is a cross-section similar to FIG. 5B, but is aligned with channels 514 in concave component 502 and channels 516 in convex component 504. Tension members 522, such as for controlling other links in an articulating system, are shown passing through channels 514 and 516. The tapering of channels 516 permit members 500, 500 to pivot without tension members 522 binding. In some embodiments of the invention, channels 516 may be tapered only at their lower ends and not at their upper ends. In other embodiments, channels 514 in concave component 502 may be tapered while channels 516 in convex component 504 are straight. In yet other embodiments, channels in both components 502 and 504 are tapered. In still other embodiments, channels in both components 502 and 504 are straight and sufficient axial distance between the channels is provided to inhibit binding of tension members 522 during pivoting movement.

With the arrangement shown in FIG. 6B, torque may be transmitted between members 500, 500 by tension members 522 without the need for protrusions and slots as previously described in relation to FIG. 3. It can be appreciated that the shorter the distance between channels 514 and 516 and the closer that these channels constrain tension members 522, the less axial rotation or backlash there will be between members 500, 500 for a given torque.

Spherical joints constructed as described above may be provided with mating spherical surfaces that are larger than those of conventional spherical joints for a given joint envelope because they are not outwardly constrained by ball protrusions, socket slots, or tension members that are located radially outward from the mating spherical surfaces. Larger surface sizes may provide additional benefits such as being able to carry more load, allow for looser tolerance control and/or greater instrument rigidity. Such an arrangement may also allow one or more components of the joint to be made out of lighter, cheaper or disposable material such as plastic.

FIGS. 7A-7B and 8A-8E show details of convex bushing components 550 that may be used in any of the articulating devices described above. For example, components 550 may be used in pairs in a similar manner to proximal bushings 109 and 111 shown in FIG. 3, and/or in the distal articulating mechanism of a grasper instrument as shown in FIG. 16.

Figure 8A:
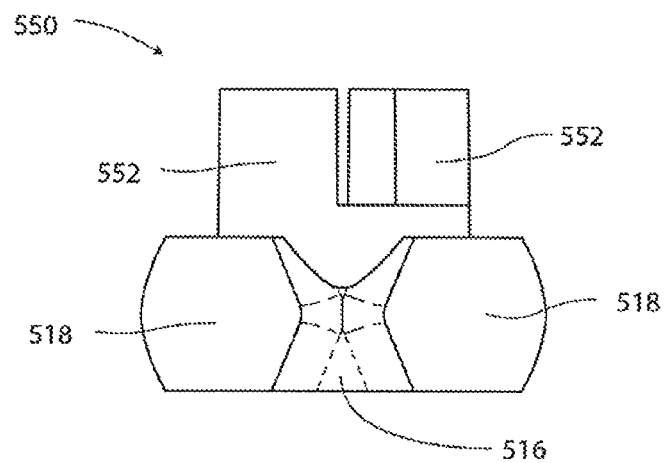
Figure 8B:
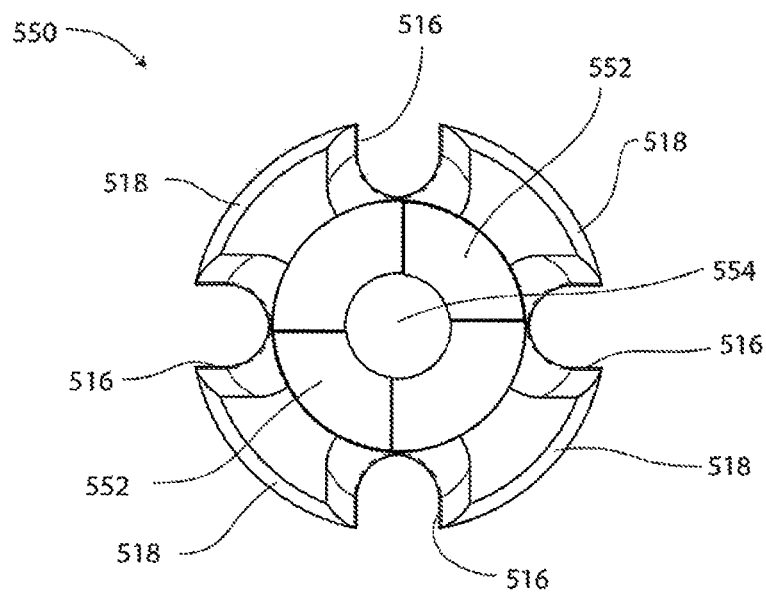
Figure 8C:
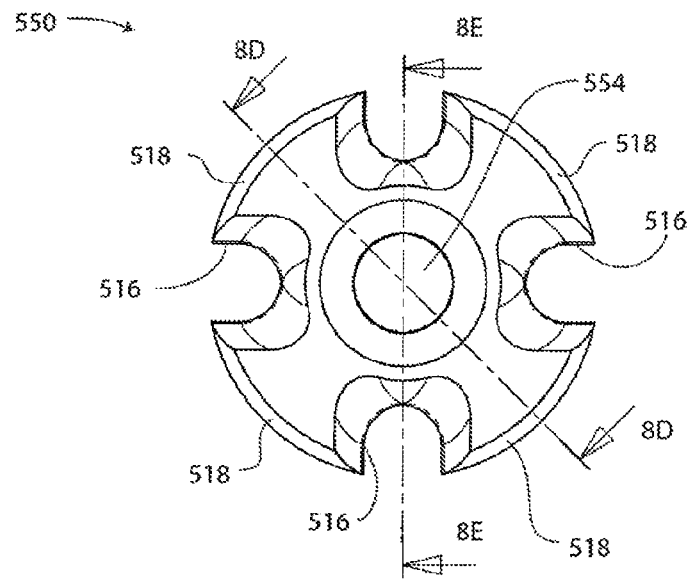
Figures 8D, 8E:
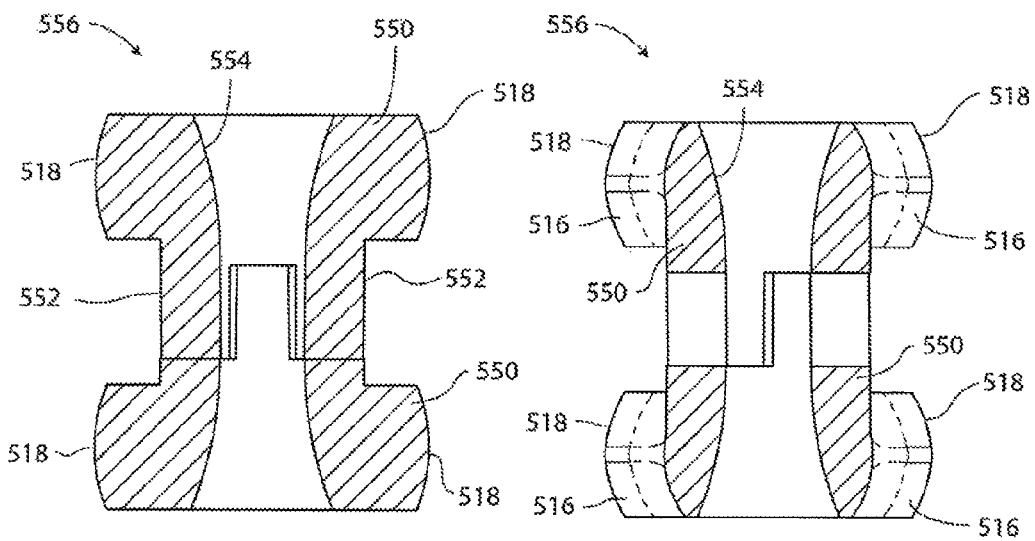

Convex components 550 are constructed and operate in a manner similar to that of convex components 504 described above. In particular, each component 550 includes a portion having the overall shape of a frustro-sphere, as best seen in FIG. 8A. This frusto-sphere is circumferentially interrupted by four channels 516 that extend axially through the frusto-sphere, but also extend radially outward to divide the frustro-sphere into four convex spherical surfaces 518. As best seen in FIG. 8A, each channel 516 is outwardly tapered at both its top and bottom to generally form an hourglass shape.

Figure 9:
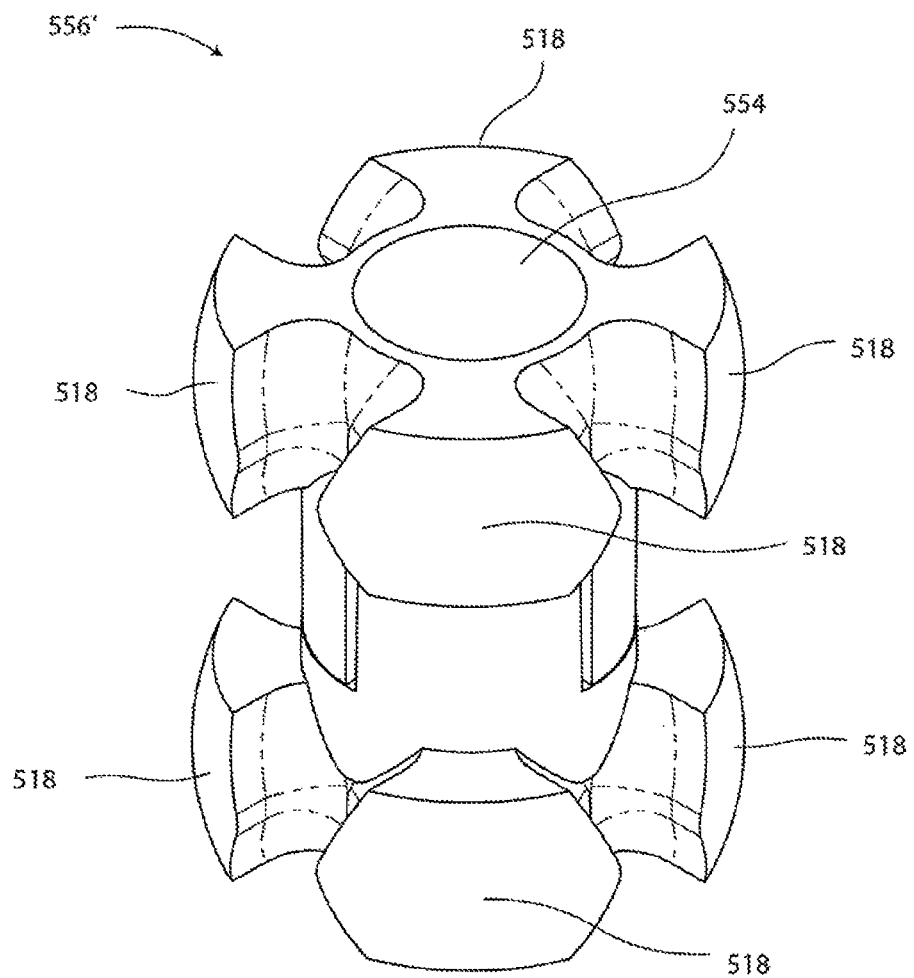
FIG. 9 shows details of a double-ended convex bushing component formed as a single unitary piece.
Figure 11A:
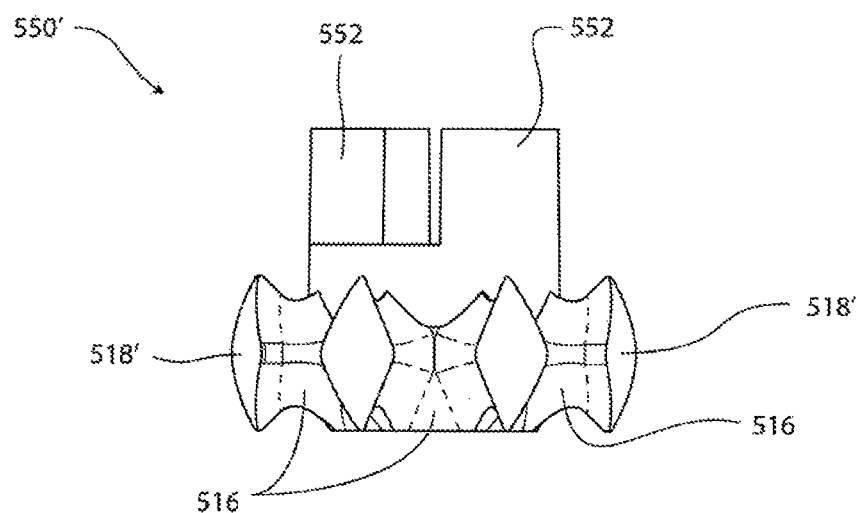
Figure 11B:
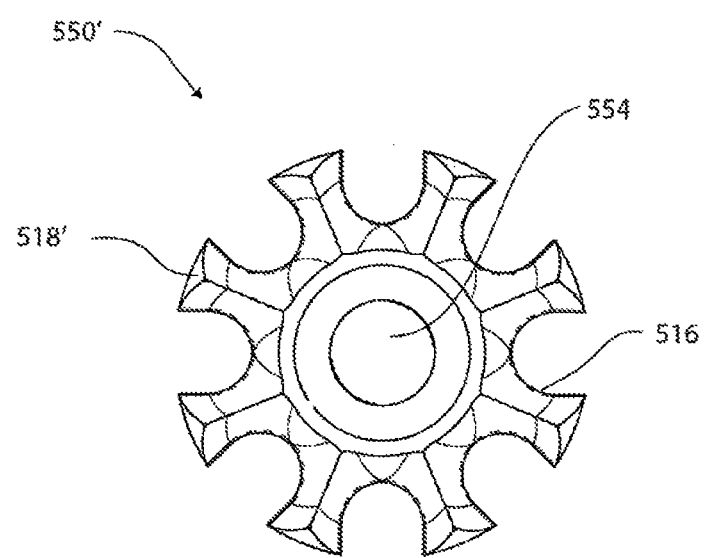

Each convex component 550 comprises a pair of opposing, axially protruding ring segments 552 on opposite sides of a central bore 554, as best seen in FIG. 7A where two components 550 are shown axially separated. The protruding ring segments 552 of two facing components 550 may be rotationally oriented as shown in FIG. 7A so that when they are axially drawn together, as shown in FIG. 7B, the four protruding ring segments 552 interdigitate and rotationally lock the two components 550 together. This creates a double-ended bushing 556, with each end having a convex component formed by four spherical surfaces 518. Forming the double-ended bushing 556 from two separate pieces as shown facilitates fabrication of the bushing from an injection molding process. As shown in FIG. 9, a similar double-ended bushing 556' may also be formed as a single, unitary piece.

FIGS. 10A-10B and 11A-11B show details of convex bushing components 550'. Convex components 550' are similar to convex components 550 described above and shown in FIGS. 7A-7B and 8A-8E, except that components 550' each have eight channels 516 instead of four channels 516. This allows up to eight tension members 522 (shown in FIG. 6B) to pass through components 550'. When two convex bushing components 550' are interengaged as shown in FIG. 10B, they form a double-ended bushing 556", with each end having a convex component formed by eight spherical surfaces 518'. A similar double-ended bushing (not shown) may also be formed as a single, unitary piece.

Figure 15:
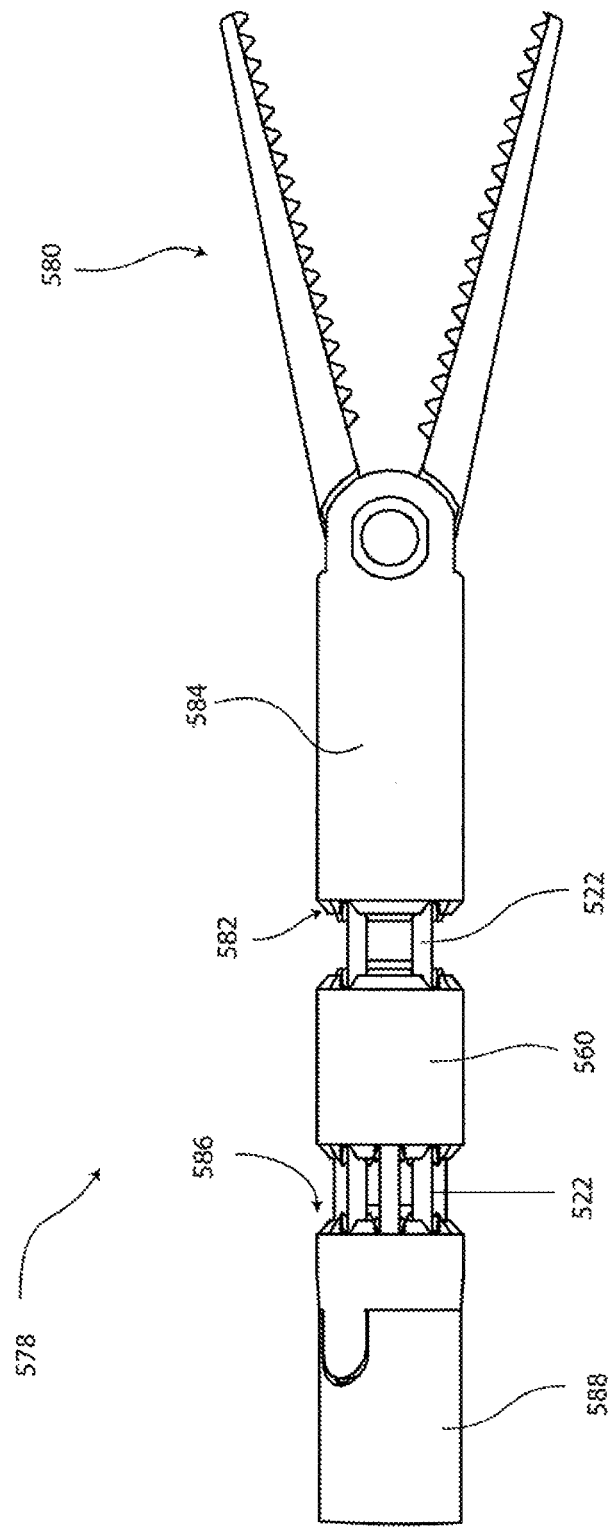
Figure 17A:
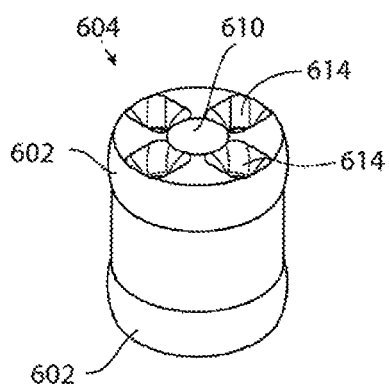
Figure 17B:
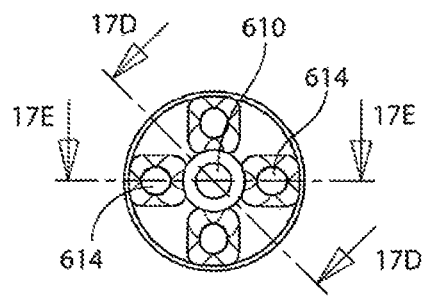
Figure 17C:
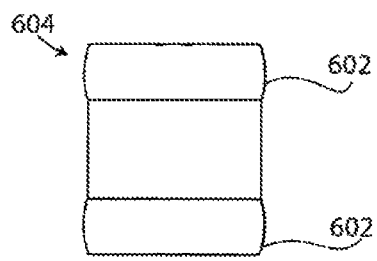
Figure 17D:
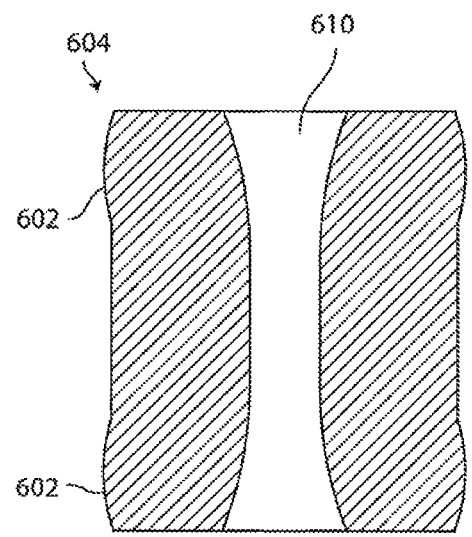
Figure 17E:
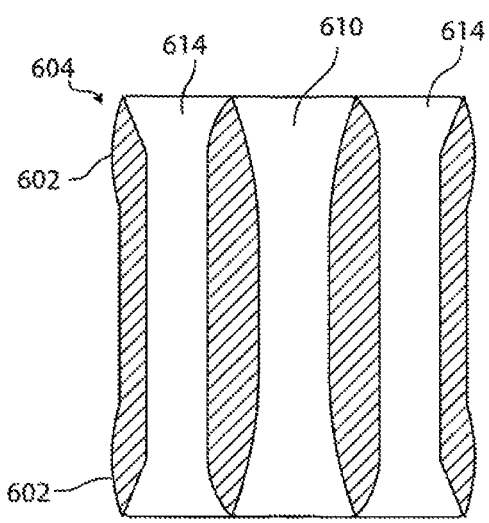

FIGS. 12A-12B and 13A-13C show details of a concave link member 560 that may be used in the articulating devices described above. For example, members 560 may be used in a similar manner to proximal links 108 and 110 shown in FIG. 3, and/or in the distal articulating mechanism of a grasper instrument as shown in FIGS. 15 and 16.

Concave member 560 is constructed and operates in a manner similar to that of concave component 502 described above. In particular, a central axial bore 506 may be provided through member 560. A recess having a concave spherical surface 508 is provided at each end of concave member 560. In this embodiment, each spherical surface 508 is bounded on the outside by a castellated rim surface 562 or 564, and on the inside by a stop surface 566 or 568. Rim surfaces 562 and 564 are castellated in order to provide clearance for the tension members 522 when the device is articulated. Stop surfaces 566 and 568 function in a manner similar to previously described stop surface 512. Each concave spherical surface 508 is interrupted by the openings of eight channels 570 that travel axially through concave member 560 and in this embodiment are evenly spaced around the central axial bore 506.

Figure 12A:
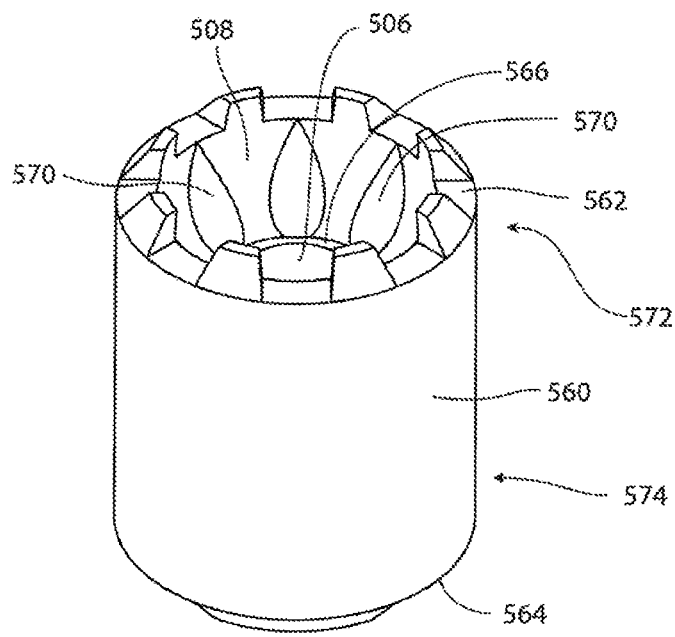
FIGS. 12A, 12B, and 13A, 13B, 13C show details of a concave link member for use with an articulating device.
Figure 12B:
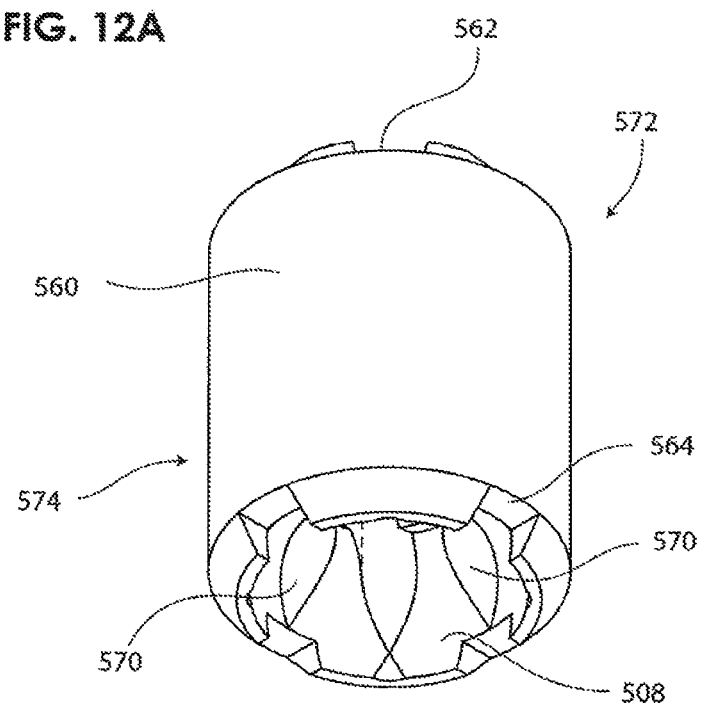
Figure 13A:
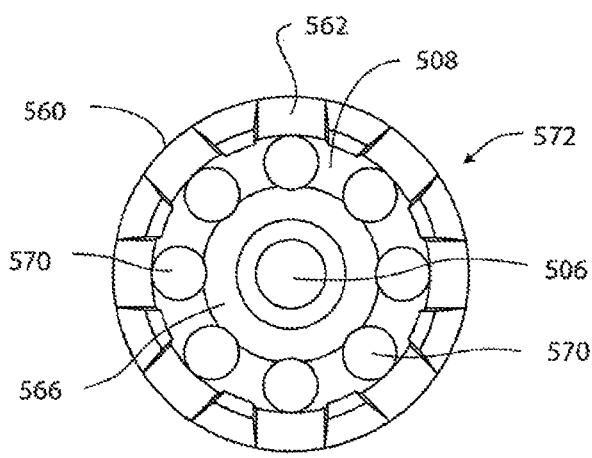
Figure 13B:
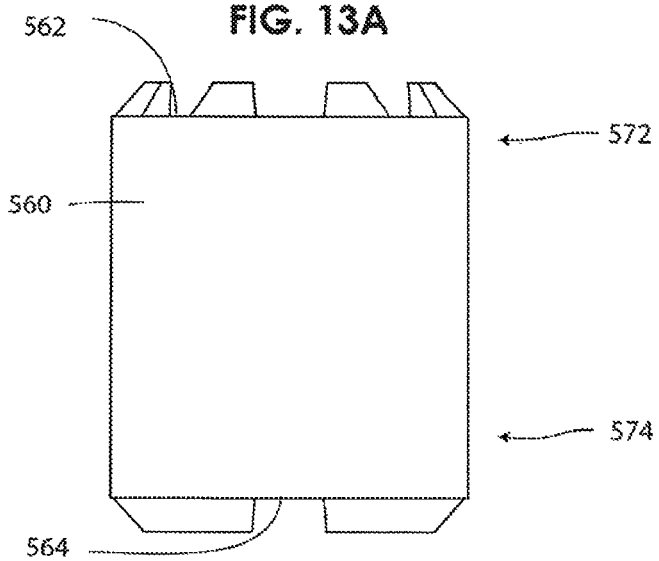

The recess and spherical surface 508 located on the proximal end 572 of member 560 (as shown in FIGS. 12A and 13A) are configured to pivotably engage with the convex spherical surfaces 518' formed on one end of a convex bushing component 550' (shown in FIGS. 10A-10B and 11A-11B). Similarly, the recess and spherical surface 508 located on the distal end 574 of member 560 (as shown in FIGS. 12B and 13C) are configured to pivotably engage with the convex spherical surfaces 518 formed on one end of a convex bushing component 550 (shown in FIGS. 7-9).

Figure 13C:
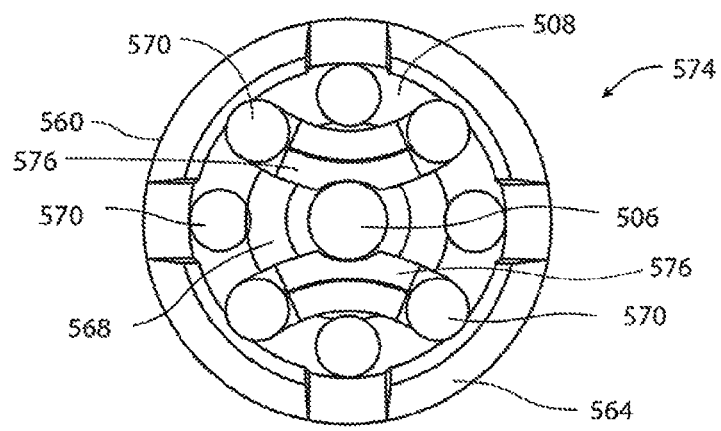

As shown in FIG. 13C, the recess located on the distal end 574 of member 560 is provided with two cross channels 576 that interconnect the distal ends of every other channel 570. This allows a tension member 522 (not shown in FIG. 13) to pass through one channel 570 from the proximal end 572 to the distal end 574 of member 560, cross over to another channel 570, and return to the proximal end 572 through the other channel 570. Surface friction (or in some embodiments, adhesive, solder, crimping, or the like) keeps tension members 522 from sliding in cross channels 576. In this manner, the four tension member portions that extend through the four channels 570 connected to cross channels 576 can be used to control the pivoting motion of concave link member 560, while four other tension members 522 can pass through member 560 in the remaining four channels 570 to control another link located distal to member 560, as will be more fully described below.

FIGS. 14A-14C show details of a concave link member 560'. Member 560' is similar in construction and operation to that of member 560, except member 560' has only four axial channels 570 through it instead of eight.

FIGS. 15 and 16 show details of the distal end of an articulating instrument, similar to instrument 100 shown in FIGS. 1-3 and having a distal articulating mechanism 578 similar to the articulating mechanism shown in FIG. 2B. The distal end of the instrument includes a pair of graspers 580 that may be operated by an actuator (not shown) located at the proximal end of the instrument.

Distal articulating mechanism 578 includes a double-ended convex bushing 556, a concave link member 560, and a double-ended convex bushing 556", all as previously described. A distal link 582, constructed in a similar manner to one half of concave link member 560 shown in FIGS. 14A-14C, may be formed on grasper housing 584. Similarly, a recess 586, constructed in a similar manner to the proximal end 572 of concave member 560 shown in FIGS. 12-13, may be provided on the distal end of instrument shaft 588. With this arrangement, concave distal link 582 may pivot relative to concave link member 560 about the centers of the two spherical ends of double-ended convex bushing 556. Similarly, concave link member 560 may pivot relative to recess 586 about the centers of the two spherical ends of double-ended convex bushing 556".

An articulating mechanism similar to distal articulating mechanism 578 may be used at the proximal end of the instrument, although its relative size may be larger or smaller to provide scaling of movement. In this exemplary embodiment, one set of four tension members 522 interconnects the innermost links (i.e. distal link 560 and the proximal link (not shown in FIG. 15 or 16) closest to shaft 588). A separate set of four more tension members 522 interconnects the outermost links (i.e. distal link 582 and the proximal link (not shown in FIG. 15 or 16) farthest from shaft 588). With this arrangement, movement of the instrument handle (not shown) causes movement of the two proximal links which in turn drive corresponding movement of their respective distal links 560 and 582 directly through movement of the associated tension members 522.

FIGS. 17-20 show details of an alternative embodiment of articulating mechanism 600. The construction and operation of mechanism 600 is similar to previously described articulating mechanism 578, but the convex and concave portions have been reversed. In other words, the convex components 602 are located on the links 604, and the concave components 606 are located on the bushings 608. As previously described, each of the components may be provided with a central axial bore 610 and 612, respectively, which may be tapered at one or both ends. Additionally, axial channels 614 in links 604 and axial channels 616 in bushing 608 for receiving tension members 522 may be tapered at one or both ends. As best seen in FIGS. 18A and 18B, the tension member channels 616 in bushing 608 may be elongated such that they form a single cross-shaped opening with central bore 612.

As with the previous embodiments described, articulating mechanism 600 is able to transmit torque between the links 604 and bushings 608 through tension members 522 without the use of other torque transmitting features on the components. In other embodiments (not shown), articulating joints may be configured such that torque is not readily transmitted between the components by tension members 522, but other advantages are nonetheless conferred by locating the tension members through one or more mating spherical surfaces of the joints.

While the inventive surgical instruments and devices with improved articulating mechanisms have been described in some detail by way of illustration, such illustration is for purposes of clarity of understanding only. It will be readily apparent to those of ordinary skill and in the art in light of the teachings herein that certain changes and modifications may be made thereto without departing from the spirit and scope of the appended claims. For example, while the tool embodiments described in here have typically been in the context of tools with an articulating mechanism comprising at least two links, the tension member guide system may be used in an instrument comprising only a single link, a multiplicity of links, and with any number of tension members such as cables, or numbers of cable sets operably connecting the links. Further, the tension member guide system may be used in tools that are absent various features that may be associated with some articulatable instruments, such as handles, rotatability features, and dedicated end effectors. Finally, while the context of the invention may be considered to be surgical or medical diagnostic procedures, devices having such an articulation system may have utility in other non-medical contexts as well.

What is claimed is:

1. An articulating mechanism comprising:
   a joint having a central longitudinal axis extending therethrough, the joint including a first linking member having a convex component and a second linking member having a mating concave component sized to receive at least a portion of the convex component,
   wherein the convex component includes a frusto-spherical portion;
   wherein the concave component includes a spherical surface defining a cavity within the concave component and includes a frustoconical base surface extending around the central longitudinal axis and protruding from the spherical surface into the cavity, the base surface being non-perpendicular to the central longitudinal axis to limit angular rotation between the convex component and the mating concave component, wherein each of the convex and concave components includes a plurality of channels, the channels in the concave component having an opening located on the spherical surface;

a set of tension members, wherein individual tension members from the set of tension members extend through each of the plurality of channels to transmit motion between the mating convex and mating concave components;

wherein the plurality of channels of the convex component divide the frusto-spherical portion into a plurality of separate segments, each segment defining a frusto-spherical surface portion; and wherein each of the plurality of channels of the convex component is respectively outwardly tapered from a mid-section of the channel to a first end and a second end of the channel.

2. The articulating mechanism of claim 1 wherein each of the convex and concave components comprises a central axial bore therethrough.

3. The articulating mechanism of claim 1 wherein the joint is connected to a paired joint by the set of tension members such that motion of the joint causes corresponding motion of the paired joint.

4. The articulating mechanism of claim 3 wherein the joint and paired joint are interconnected by a discrete plurality of tension members of the set of tension members.

5. The articulating mechanism of claim 3 further comprising a spacer component extending between the joint and its paired joint, the spacer component including a channel sized to receive the set of tension members therethrough wherein the spacer component further comprises a central axial bore therethrough.

6. The articulating mechanism of claim 1 wherein
the first linking member includes the convex component of the joint integrally formed with a concave component of a first adjacent joint.

7. The articulating mechanism of claim 6 wherein
the second linking member includes the mating concave component of the joint integrally formed with a convex component of a second adjacent joint.

8. The articulating mechanism of claim 1 wherein the first linking member includes a spacer component that comprises a pair of opposing ring segments on opposite sides of a central axial bore that extends through the spacer component along the central axial component.

9. The articulating mechanism of claim 1 wherein
the first linking member includes a first end including the convex component of the joint and a second end including a convex component of a first adjacent joint.

10. The articulating mechanism of claim 1 wherein
the second linking member includes a first end including the concave component of the joint and a second end including a concave component of a first adjacent joint.

11. The articulating mechanism of claim 1 wherein the base surface is symmetrical with respect to the central longitudinal axis.

* * * * *